(12) United States Patent
Chen

(10) Patent No.: US 12,239,403 B2
(45) Date of Patent: Mar. 4, 2025

(54) TERMINAL MECHANISM OF SURGICAL ROBOT AND CONTROL METHOD AND RELATED EQUIPMENT THEREOF

(71) Applicant: Eabmed Science and Technology (Shanghai) Co., Ltd., Shanghai (CN)

(72) Inventor: Yi Chen, Shanghai (CN)

(73) Assignee: Eabmed Science and Technology (Shanghai) Co., Ltd., Shanghai (CN)

( * ) Notice: Subject to any disclaimer, the term of this patent is extended or adjusted under 35 U.S.C. 154(b) by 0 days.

(21) Appl. No.: 18/702,634

(22) PCT Filed: Oct. 13, 2022

(86) PCT No.: PCT/CN2022/125100
§ 371 (c)(1),
(2) Date: Apr. 18, 2024

(87) PCT Pub. No.: WO2023/082929
PCT Pub. Date: May 19, 2023

(65) Prior Publication Data
US 2024/0407870 A1 Dec. 12, 2024

(30) Foreign Application Priority Data
Nov. 12, 2021 (CN) .......................... 202111338460.1

(51) Int. Cl.
*B25J 15/00* (2006.01)
*A61B 34/00* (2016.01)
(Continued)

(52) U.S. Cl.
CPC .............. *A61B 34/35* (2016.02); *A61B 34/70* (2016.02); *A61B 2034/305* (2016.02)

(58) Field of Classification Search
CPC ......... A61B 34/35; A61B 34/37; A61B 34/70; A61B 34/74; A61B 34/71;
(Continued)

(56) References Cited

U.S. PATENT DOCUMENTS 9,717,563 B2 * 8/2017 Tognaccini ............ A61B 1/018
10,258,425 B2 * 4/2019 Mustufa ................ A61B 34/37
(Continued)

FOREIGN PATENT DOCUMENTS

| CN | 104758060 A | 7/2015 |
|----|-------------|--------|
| CN | 104958085 A | 10/2015 |

(Continued)

OTHER PUBLICATIONS

Abbott et al., Design of an endoluminal NOTES robotic system, 2007, IEEE, p. 410-416 (Year: 2007).*
(Continued)

*Primary Examiner* — McDieunel Marc
(74) *Attorney, Agent, or Firm* — Woodard, Emhardt, Henry, Reeves & Wagner, LLP

(57) ABSTRACT

A terminal mechanism of a surgical robot and control method and related equipment thereof. The control method comprises: generating a pose adjustment signal upon a remote center of motion and a spatial target point, for a robotic arm to drive an instrument base until the remote center of motion coincides with the target point; generating an extension signal for a positioning link to extend until the distal center of a channel member coincides with the remote center of motion; monitoring an installation completion signal of an surgical instrument at an instrument driving mechanism, and if yes, generating an instrument movement signal to move the surgical instrument to the target position. The surgical robot is suitable for few-port or single-port surgery. By controlling its terminal mechanism, interfer-
(Continued)

ences of end components are avoided, control accuracy is improved, and stability and availability is ensured.

14 Claims, 19 Drawing Sheets

(51) Int. Cl.
 *A61B 34/35* (2016.01)
 *A61B 34/30* (2016.01)
(58) Field of Classification Search
 CPC ........ A61B 2090/066; A61B 2034/305; A61B 17/29; A61B 34/30; A61B 2090/064; A61B 2034/2059; B25J 15/0028
 See application file for complete search history.

(56) References Cited

U.S. PATENT DOCUMENTS

| | | | |
|---|---|---|---|
| 10,820,949 B2* | 11/2020 | Prisco | .................... A61B 34/30 |
| 2013/0197541 A1 | 8/2013 | Schena | |
| 2018/0049828 A1* | 2/2018 | Robinson | ............... A61B 34/76 |
| 2018/0126546 A1 | 5/2018 | Vaders | |
| 2020/0246092 A1* | 8/2020 | Robinson | ............... A61B 34/30 |
| 2021/0282874 A1* | 9/2021 | Hussain | ................ A61B 90/39 |

FOREIGN PATENT DOCUMENTS

| | | | |
|---|---|---|---|
| CN | 106974732 | A | 7/2017 |
| CN | 107148250 | A | 9/2017 |
| CN | 109330700 | A | 2/2019 |
| CN | 110811838 | A | 2/2020 |
| CN | 111345894 | A | 6/2020 |
| CN | 111481243 | A | 8/2020 |
| CN | 112274249 | A | 1/2021 |
| CN | 212281453 | U | 1/2021 |
| CN | 114098977 | A | 3/2022 |
| CN | 114098978 | A | 3/2022 |

OTHER PUBLICATIONS

Hagn et al., Telemanipulator for remote minimally invasive surgery, 2008, IEEE, p. 1-11 (Year: 2008).*
Hu et al., In-vivo pan/tilt endoscope with integrated light source, 2007, IEEE, p. 1284-1289 (Year: 2007).*
Choi et al., Linkage-driven manipulator with embedded ultrasonic motors, 2012, IEEE, p. 899-904 (Year: 2012).*

* cited by examiner

TERMINAL MECHANISM OF SURGICAL ROBOT AND CONTROL METHOD AND RELATED EQUIPMENT THEREOF

FIELD OF THE DISCLOSURE

The present invention relates to the technical field of medical devices, and specifically to a terminal mechanism of a surgical robot and control method and related equipment thereof.

BACKGROUND

With the advancement of science and technology, surgical robot technology for minimally invasive surgery has gradually matured and been widely used. However, current surgical robots are mostly used for multi-port surgeries and cannot meet the needs of few-port or single-port surgeries. In addition, current surgical robots are prone to interference between end components, affecting their usability, and the control accuracy does not meet the requirements to ensure the stability and availability of the robot system.

It should be noted that the information disclosed in the background section above is only used to enhance understanding of the background of the present invention, and therefore may include information that does not constitute prior arts known to those of ordinary skill in the art.

SUMMARY OF THE INVENTION

In view of this, the present invention provides a terminal mechanism of a surgical robot, its control method and related equipment, which are suitable for minimally invasive surgery with few ports or a single port, and can avoid interference of end parts, improve the control accuracy, and ensure the stability and availability of the surgical robot.

According to one aspect of the present invention, a terminal mechanism of a surgical robot is provided, comprising: an instrument base, connected to a distal end of a robotic arm of the surgical robot, wherein the robotic arm is configured to drive the instrument base to perform pose adjustment movements relative to a remote center of motion defined by the robotic arm; and, a positioning link, configured to telescope along a Z-axis, and connected to the instrument base, wherein a distal end of the positioning link is configured to hold a channel member, and the channel member is provided with multiple channels, and each channel extends along the Z-axis, and a distal center of the channel member faces the remote center of motion along the Z-axis; and, an instrument driving mechanism, configured to install and drive multiple surgical instruments and connected to the instrument base, wherein multiple instrument installation paths and driving paths of the instrument driving mechanism do not interfere with each other, and when the instrument driving mechanism is installed with multiple surgical instruments, instrument shafts of the multiple surgical instruments extend along the Z-axis and align with the multiple channels respectively.

In some embodiments, the channel member comprises: a hollow shell, clamped to the distal end of the positioning link through a connecting buckle; and, a proximal end plate and a distal end plate, respectively provided at a proximal end of the hollow shell facing the positioning link and a distal end away from the positioning link, wherein the proximal end plate and the distal end plate are respectively provided with through-hole arrays constituting the multiple channels; and wherein each through-hole array is distributed in a same height layer referring to a Y-axis to form a one-row array along an X-axis, or, each through-hole array is distributed in multiple height layers referring to a Y-axis to form a multiple-row array with each row of through-holes arranged along an X-axis.

In some embodiments, the surgical instrument comprises: an instrument shaft, connected to the instrument driving mechanism through a transmission device; and, an actuator base, provided at a distal end of the instrument shaft and installed with an end effector, wherein the end effector is connected to the actuator base through a drive shaft, wherein the drive shaft is a pitch shaft extending along an X-axis, or a deflection shaft extending along a Y-axis; and, a movable connecting section, located between the instrument shaft and the actuator base, and connected to the instrument shaft and the actuator base through movable joints respectively, wherein the movable joints have freedoms of movement around the X-axis, the Y-axis and the Z-axis; wherein, in an initial state, the instrument shaft, the actuator base and the movable connecting section are coaxial, and with the moving of the movable joints, a spatial position of the actuator base changes while its posture remains unchanged.

In some embodiments, the instrument driving mechanism comprises multiple instrument driving modules used to install and drive the multiple surgical instruments respectively, and the multiple instrument driving modules are connected to the instrument base by multiple moving mechanisms respectively, and the moving mechanisms are configured to drive the instrument driving modules to move along the Y-axis and the Z-axis respectively; wherein, the pose adjustment movements comprise a pitch movement and a yaw movement around a vertical rotation axis passing through the remote center of motion.

In another aspect of the present invention, a control method for a terminal mechanism of a surgical robot is provided, which is applicable to the terminal mechanism according to any one of the above-mentioned embodiments, and comprises: generating a pose adjustment signal for controlling the robotic arm according to a positional relationship between the remote center of motion and a spatial target point, so that the robotic arm drives the instrument base to perform the pose adjustment movements, until the remote center of motion coincides with the spatial target point; and, generating an extension signal to control the positioning link after executing the pose adjustment signal, so that the positioning link extends, until the distal center of the channel member coincides with the remote center of motion; and, monitoring whether there is an installation completion signal of a surgical instrument at the instrument driving mechanism after executing the extension signal; and, if yes, generating instrument movement signals to move the surgical instrument to a target position.

In some embodiments, the instrument driving mechanism is configured to move along the Z-axis, and a distal end of an instrument shaft is provided with an actuator base, and the actuator base is connected with an end effector; and, said generating instrument movement signals comprises: generating a first forward signal for controlling the instrument driving mechanism, so that the instrument driving mechanism drives the surgical instrument to advance along the Z-axis until the end effector passes through a corresponding channel.

In some embodiments, the end effector and the actuator base are connected through a drive shaft, and the drive shaft is a pitch shaft extending along an X-axis or a deflection shaft extending along a Y-axis, and the first forward signal is used to advance the surgical instrument until the drive shaft passes through the corresponding channel; and, said generating instrument movement signals further comprises: after executing the first forward signal, generating a folding signal to control the end effector, so that the end effector performs a folding movement by a preset angle around the drive shaft; wherein, when the drive shaft is a pitch shaft, the folding movement is a first pitch movement around the pitch shaft, and when the drive shaft is a deflection shaft, the folding movement is a first deflection movement around the deflection shaft.

In some embodiments, a movable connecting section is connected between the instrument shaft and the actuator base, and in an initial state, the movable connecting section is coaxial with the instrument shaft and the actuator base; and, said generating instrument movement signals further comprises: after executing the folding signal, generating a second forward signal to control the instrument driving mechanism, so that the instrument driving mechanism drives the surgical instrument to advance along the Z-axis until the movable connecting section passes through the corresponding channel.

In some embodiments, movable joints are provided between the movable connecting section and the instrument shaft, and between the movable connecting section and the actuator base respectively, and the movable joints have freedoms of movement along the X-axis, the Y-axis and the Z-axis, and the second forward signal is used to advance the surgical instrument until the movable joints pass through the corresponding channel; and, said generating instrument movement signals further comprises: after executing the second forward signal, generating a parallel unfolding signal to control the movable connecting section, so that the movable connecting section performs a parallel unfolding movement in an opposite direction of the preset angle, and during all steps of the parallel unfolding movement, the actuator base remains parallel to the instrument shaft; wherein, when the drive shaft is a pitch shaft, the parallel unfolding movement is a second pitch movement around the X-axis, and when the drive shaft is a deflection shaft, the parallel unfolding movement is a second deflection movement around the Y-axis.

In some embodiments, said generating instrument movement signals further comprises: after executing the parallel unfolding signal, generating un unfolding signal to control the end effector, so that the end effector performs an unfolding movement around the drive shaft in an opposite direction of the preset angle and by an angle equal to the preset angle, to reach the target position; wherein, when the drive shaft is a pitch shaft, the unfolding movement is a third pitch movement around the pitch shaft, and when the drive shaft is a deflection shaft, the unfolding movement is a third deflection movement around the deflection shaft.

In some embodiments, when the instrument driving mechanism is equipped with two surgical instruments, said generating an instrument movement signal further comprises: after executing the unfolding signal of each surgical instrument, generating first posture adjustment signals to control the movable connecting section and the end effector of each surgical instrument, so that the surgical instruments move to positions where tips of the end effectors are opposed to each other and are spaced from each other.

In some embodiments, when the instrument driving mechanism is equipped with three surgical instruments, said generating an instrument movement signal further comprises: after executing the unfolding signal of each surgical instrument, generating second posture adjustment signals to control the movable connecting section and the end effector of each surgical instrument, so that the surgical instruments move to positions where tips of the end effectors are opposed to each other and constitute a spatial triangle.

In some embodiments, the pose adjustment signal, the extension signal and the equipment movement signals are all configured to be interruptible, wherein when a signal is interrupted, a corresponding execution of the signal is paused, until when a continuing signal is detected, the corresponding execution of the signal is continued; and, during execution of a current signal, an execution status of an executing object is monitored, wherein, when the execution status of the executing object is abnormal, an execution completion status of a preceding signal of the current signal is returned to, to wait for a re-execution control signal; and, after execution of the current signal, a corresponding executing object is locked and waits for a subsequent signal.

In some embodiments, the instrument driving mechanism is configured to move along a Y-axis and the Z-axis, and an end effector is provided at a distal end of an instrument shaft, and spatial positions in the Y-axis and in the Z-axis of the end effector are variable; and, said generating instrument movement signals comprises: generating a first movement signal to control the surgical instrument, so that the end effector moves along a plane defined by the Y-axis and the Z-axis, to a predefined configuration relative to the instrument shaft; and, after executing the first movement signal, generating a second movement signal to control the instrument driving mechanism, so that the instrument driving mechanism drives the surgical instrument to move along the plane defined by the Y-axis and the Z-axis until the end effector and the distal end of the instrument shaft pass through a corresponding channel and reach the target position.

In some embodiments, the control method further comprising: generating a retraction signal to control the positioning link when the surgical instrument moves to the target position, so that the positioning link is retracted until the distal center of the channel member faces the remote center of motion.

In another aspect of the present invention, a control device for a terminal mechanism of a surgical robot is provided. The control device is used to implement the control method according to any one of the above-mentioned embodiments. The control device comprises: a robotic arm control module, configured to generate the pose adjustment signal to control the robotic arm according to a positional relationship between a remote center of motion and a spatial target point, so that the robotic arm drives the instrument base to perform the pose adjustment movements, until the remote center of motion coincides with the spatial target point; and, a positioning link control module, configured to generate the extension signal to control the positioning link after executing the posture adjustment signals, so that the positioning link extends, until the distal center of the channel member coincides with the remote center of motion; and, a surgical instrument control module, configured to monitor whether there is an installation completion signal of a surgical instrument at the instrument driving mechanism after executing the extension signal, and if yes, to generate the instrument movement signals to move the surgical instrument to the target position.

In another aspect of the present invention, an electronic device is provided, comprising: a processor; a memory, stored with executable instructions; wherein, when the executable instructions are executed by the processor, the control method for a terminal mechanism of a surgical robot according to any one of the above-mentioned embodiments is implemented.

In another aspect of the present invention, a computer-readable storage medium used to store a program is provided. When the program is executed by a processor, the control method for a terminal mechanism of a surgical robot according to any one of the above-mentioned embodiments is implemented.

Compared with the prior arts, the beneficial effects of the present invention at least include the following ones.

The surgical robot of the present invention is suitable for few-port or single-port surgeries. And by controlling the terminal mechanism of the surgical robot, interferences of end parts can be avoided, control accuracy can be improved, and the stability and availability of the surgical robot can be ensured. And damages to the surgical robot can be avoided, also ensuring the safety of the surgical robot during use and improving the convenience of use.

It should be understood that the above general description and the following detailed description are exemplary and explanatory only, and do not limit the present invention.

BRIEF DESCRIPTION OF THE DRAWINGS

The accompanying drawings, which are incorporated in and constitute a part of this specification, illustrate embodiments consistent with the invention and together with the description serve to explain the principles of the invention. Obviously, the drawings described below are only some embodiments of the present invention. For those of ordinary skill in the art, other drawings can be obtained based on these drawings without exerting creative efforts.

DESCRIPTION OF THE ILLUSTRATED EMBODIMENTS

Figure 1:
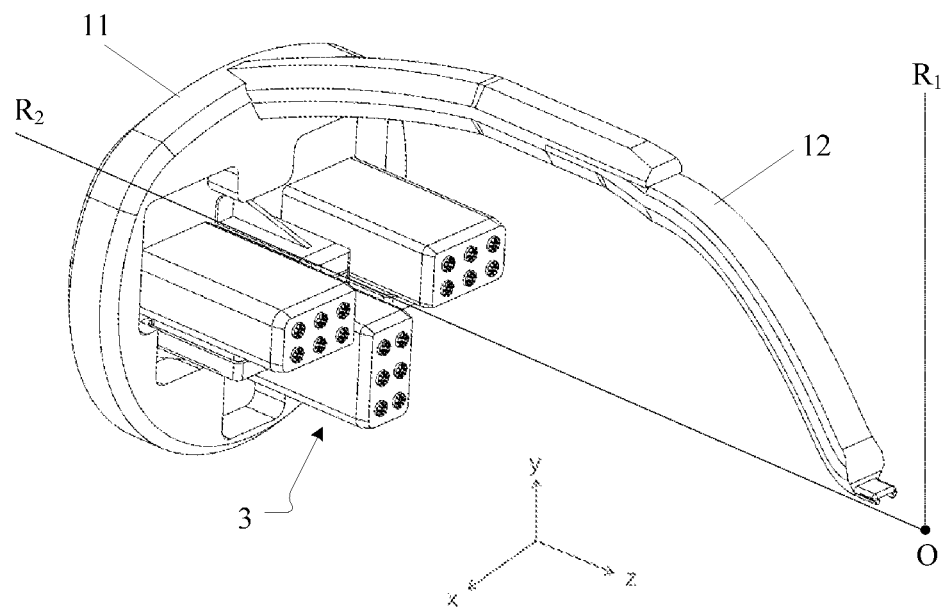
FIG. 1 shows a schematic diagram of a terminal mechanism of a surgical robot in an embodiment of the present invention.

Example embodiments will now be described more specifically with reference to the accompanying drawings. Example embodiments may, however, be embodied in various forms and should not be construed as limited to the embodiments set forth herein. Rather, these embodiments are provided so that this disclosure will be thorough and complete, and will fully convey the concept of example embodiments to those skilled in the art.

The drawings are merely schematic illustrations of the invention and are not necessarily drawn to scale. The same reference numerals in the drawings represent the same or similar parts, and thus their repeated description will be omitted. Some of the block diagrams shown in the figures are functional entities and do not necessarily correspond to physically or logically separate entities. These functional entities may be implemented in form of software, or implemented in one or more hardware modules or integrated circuits, or implemented in different networks and/or processor devices and/or microcontroller devices.

In addition, the processes shown in the drawings are only illustrative and do not necessarily comprise all steps. For example, some steps can be decomposed, some steps can be combined or partially combined, and the actual execution order may change according to actual conditions. The use of "first", "second" and similar words in specific descriptions does not imply any order, quantity or importance, but is only used to distinguish different components. It should be noted that, as long as there is no conflict, the embodiments of the present invention and features in different embodiments can be combined with each other.

Figure 2:
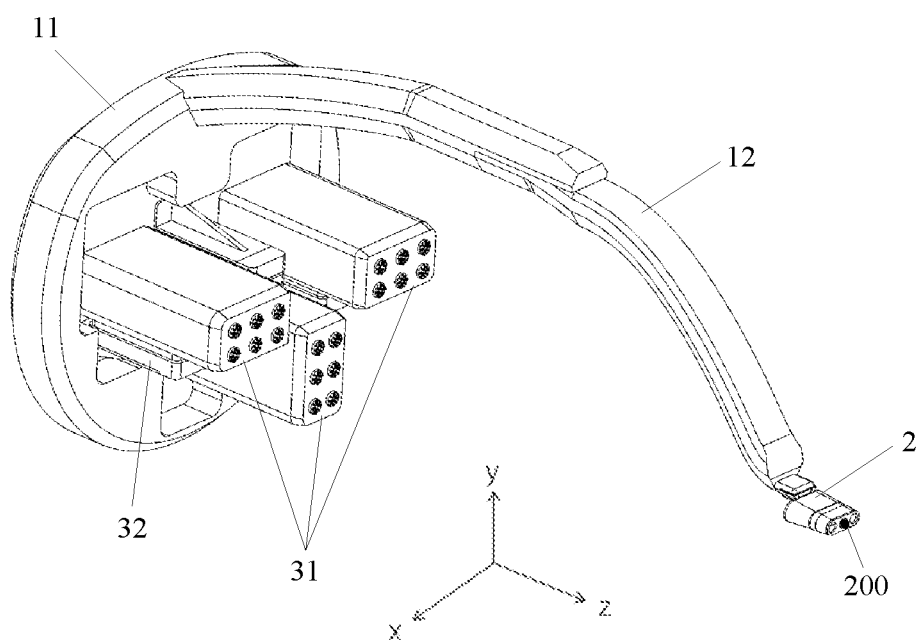
FIG. 2 shows a schematic diagram of a terminal mechanism clamping a channel member in an embodiment of the present invention.

FIG. 1 shows the structure of a terminal mechanism of a surgical robot in one embodiment, and FIG. 2 shows the structure of the terminal mechanism holding a channel member 2. Referring to FIG. 1 and FIG. 2, the terminal mechanism of the surgical robot comprises: an instrument base 11, connected to the end of the robotic arm of the surgical robot (not specifically shown in the figure). The robotic arm can drive the instrument base 11 to perform pose adjustment movements relative to a remote center of motion O defined by the robotic arm. A positioning link 12 is connected to the instrument base 11 and can telescope along a Z-axis. The distal end of the positioning link 12 can clamp the channel member 2. The channel member 2 is provided with multiple channels. Each channel extends along the Z-axis. And the distal center 200 (i.e., the geometric center of the distal end plate of the channel member 2) of the channel member 2 faces the remote center of motion O along the Z-axis. An instrument driving mechanism 3, which can install and drive multiple surgical instruments, is connected to the instrument base 11. Multiple instrument installation paths and driving paths of the driving mechanism 3 do not interfere with each other. When the instrument driving mechanism 3 is equipped with multiple surgical instruments, the instrument shafts of the multiple surgical instruments extend along the Z-axis and are aligned with the multiple channels.

The remote center of motion O is specifically defined by the intersection of a vertical rotation axis R1 of the robotic arm and a rotation axis R2 around which the instrument base 11 rotates. The pose adjustment movements comprise: driving the instrument base 11 to rotate around the X-axis, i.e. to perform a pitching movement; and to rotate around the vertical rotation axis R1, and further to rotate around the rotation axis R2. Since the vertical rotation axis R1 does not pass through the instrument base 11, the rotation around the vertical rotation axis is equivalent to a deflection movement. While the rotation axis R2 passes through the own axis of the instrument base 11, so the rotation of the instrument base 11 around the rotation axis R2 is equivalent to a rolling movement. Therefore, the pose adjustment movements of the instrument base 11 with three degrees of freedom of pitching, deflection and rolling are achieved with the remote center of motion O as a fixed point.

Figure 3:
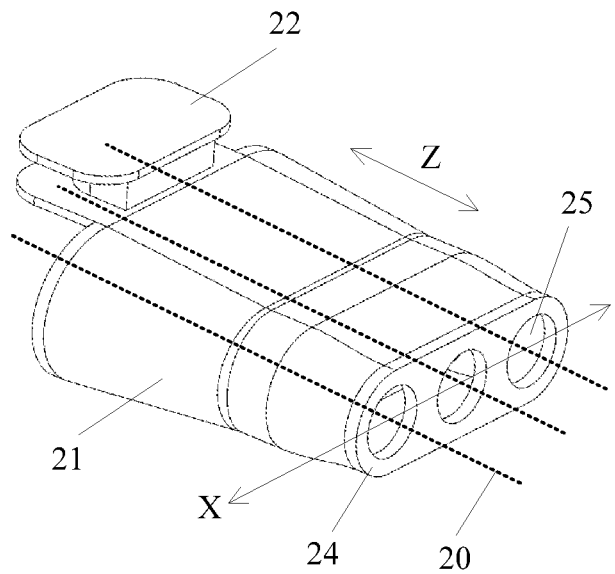
FIG. 3 and FIG. 4 show schematic diagrams of channel members in embodiments of the present invention.
Figure 4:
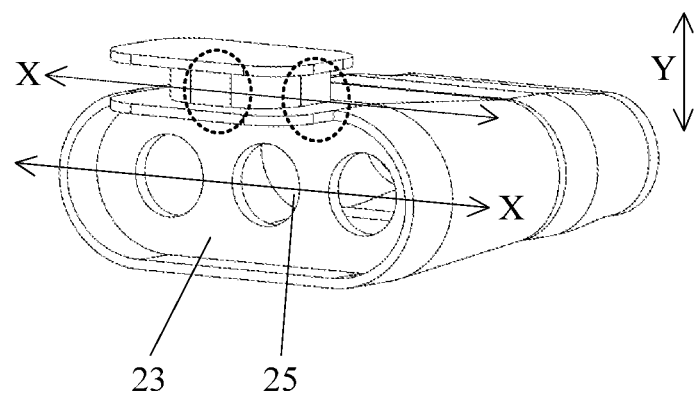

FIG. 3 and FIG. 4 show the structure of the channel member in an embodiment. As shown in FIG. 2 to FIG. 4, the channel member 2 comprises: a hollow shell 21, which is clamped to the end of the positioning link 12 through a connecting buckle 22. The proximal end plate 23 and the distal end plate 24 are respectively provided on the proximal end of the hollow shell 21 facing the positioning link 12 and on the distal end away from the positioning link 12. The proximal end plate 23 and the distal end plate 24 are respectively provided with a through-hole array 25 to constitute multiple channels 20. The through-holes of each through-hole array 25 are arranged in a same height layer referring to the Y-axis to form a single-row through-hole array arranged along the X-axis. Or the through-holes of each through-hole array 25 is staggered referring to the Y-axis. The distribution forms a multi-row through-hole array and each row of the array is arranged along the X-axis.

In FIG. 3 and FIG. 4, the through-hole arrays 25 of the proximal end plate 23 and the distal end plate 24 respectively form a single-row array with the through-holes arranged along the X-axis, that is, the through-holes in each through-hole array 25 are distributed on the same height layer referring to the Y-axis. In other embodiments, the through-holes in each through-hole array 25 can also be staggered referring to the Y-axis to form multiple rows of hole arrays and each row of hole arrays are arranged along the X-axis. And preferably, the through-holes are not aligned in the direction of the Y-axis, but are staggered from each other, forming an overall configuration of an isosceles trapezoid arrangement or a parallelogram arrangement. For example, a row of holes (shown with dotted lines) may be configured above the through-hole array 25 shown in FIG. 4, so that the entire through-hole array is arranged as an isosceles trapezoidal configuration.

The connecting buckle 22 can be a disposable sterile component. The proximal end plate 23 and the distal end plate 24 can be made of high elastic polymer materials that meet biocompatibility requirements (including but not limited to silicone rubber). Two or three or more through-hole arrays 25 may be provided on proximal end plate 23 and distal end plate 24 respectively. The through-hole arrays 25 are used to provide passages for surgical instruments and provide necessary rigid support at the distal end of the instruments. The dual support of the proximal end plate 23 and the distal end plate 24 can ensure that the instrument shafts of each surgical instrument are parallel to each other to avoid interference.

The hollow shell 21 can be made of a biocompatible high rigid polymer material (including but not limited to polycarbonate PC), and is used to provide structural support for the proximal end plate 23 and the distal end plate 24, so that they are spatially parallel to each other. The hollow shell 21 can also avoid interference between the surgical instruments and the spatial target point, which used as the reference point, when the robotic arm drives the instrument base 11 to drive the surgical instruments to perform pose adjustment movements.

Still referring to FIG. 1 and FIG. 2, the instrument driving mechanism 3 comprises a plurality of instrument driving modules 31 respectively used to install and drive a plurality of surgical instruments. The plurality of instrument driving modules 31 are respectively connected to the instrument base 11 through a plurality of moving mechanisms 32. The moving mechanism 32 can drive the instrument driving module 31 to move along the Z-axis. In addition, the moving mechanism 32 can also drive the instrument driving module 31 to move in the Y-axis perpendicular to the X-Z plane.

Figure 5:
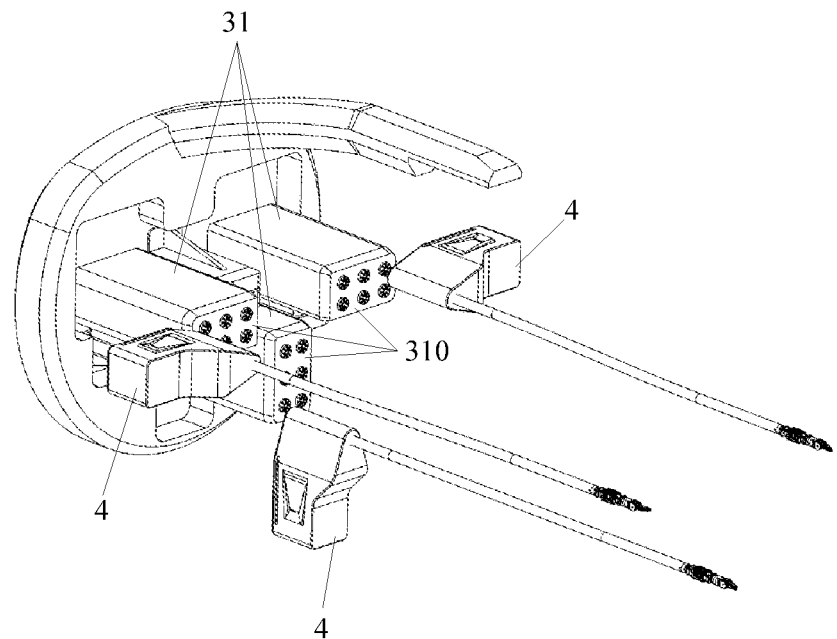
FIG. 5 and FIG. 6 show schematic diagrams of multiple instrument installation paths and driving paths of the instrument driving mechanism in an embodiment of the present invention.
Figure 6:
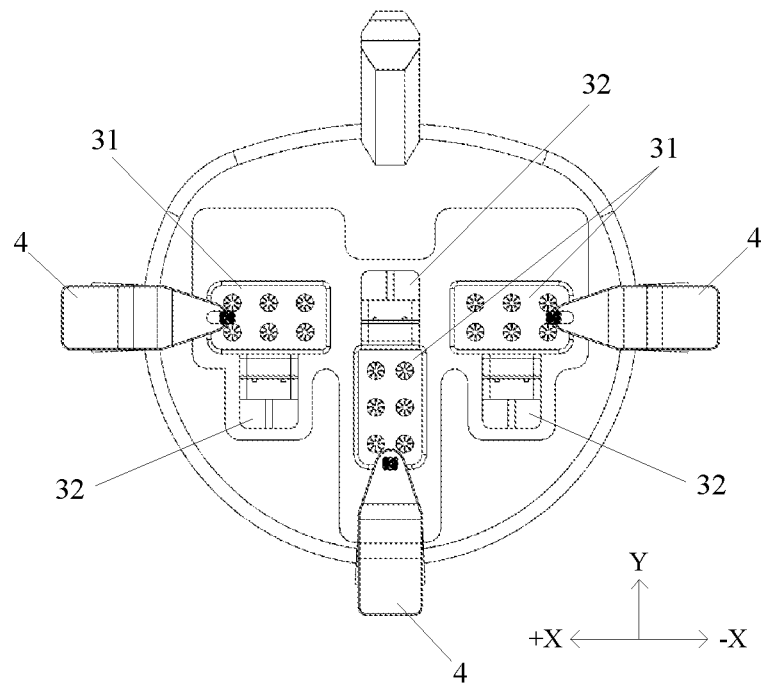
Figure 7:
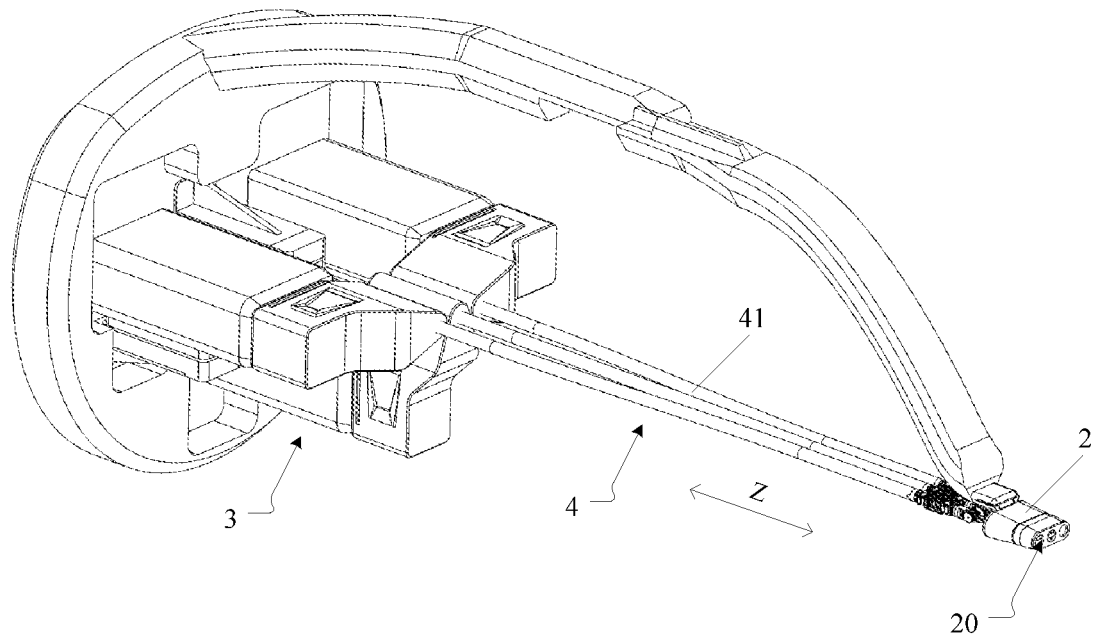
FIG. 7 shows a schematic diagram of the instrument driving mechanism equipped with three surgical instruments in an embodiment of the present invention.

FIG. 5 and FIG. 6 show multiple instrument installation paths and driving paths of the instrument driving mechanism in one embodiment. FIG. 7 shows a structure in which the instrument driving mechanism 3 is equipped with three surgical instruments. As shown in FIG. 5 to FIG. 7, when the instrument driving mechanism 3 comprises three instrument driving modules 31, three surgical instruments 4 can be installed respectively in the directions of +X-axis, −X-axis and Y-axis as shown in the figures. The installation directions are not limited to the illustration, as long as the three instrument installation paths of the instrument driving modules 31 do not interfere with each other. The three moving mechanisms 32 also do not interfere with each other in the driving paths of the three surgical instruments 4, and can drive the surgical instruments 4 along the Z-axis or the Y-axis respectively. When the instrument driving mechanism 3 is assembled with three surgical instruments 4, the instrument shafts 41 of the three surgical instruments 4 respectively extend along the Z-axis and are aligned with the plurality of channels 20 of the channel member 2.

When installed, the surgical instrument 4 is in a sterile state, and is disposable or reusable. The instrument drive module 31 may be in a non-sterile state. The instrument drive module 31 and the surgical instrument 4 are connected to each other through a drive interaction interface 310. The arrangement of the instrument driving modules 31 as shown in the figure enables each surgical instrument 4 to be independently installed, uninstalled and replaced. The surgical instrument 4 can be slid sideways in the direction of the arrows in FIG. 6 for installation, and can be slid out in the opposite directions during disassembly. After the three surgical instruments 4 are installed, their instrument shafts 41 are on the same plane and parallel to each other, and the instrument shafts 41 are separated from the channel member 2 by a certain distance. The specific types and actual number of surgical instruments 4 can be selected according to needs, and are not limited in the present invention.

Figure 8:
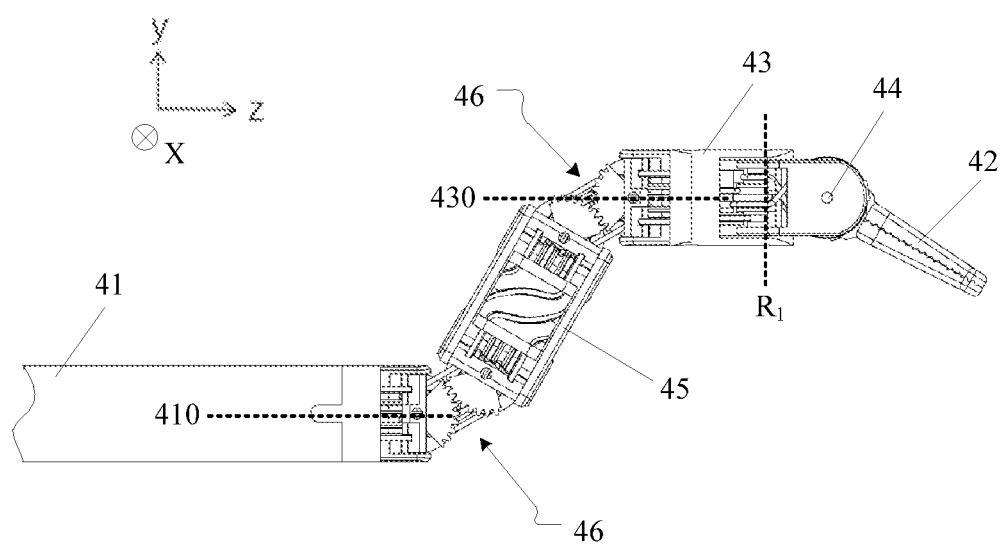
FIG. 8 shows a schematic diagram of surgical instruments in an embodiment of the present invention.

FIG. 8 shows the structure of a surgical instrument in an embodiment. As shown in FIG. 7 and FIG. 8, the surgical instrument 4 comprises an instrument shaft 41, which is connected to the instrument driving mechanism 3 through a transmission device (not specifically marked in the figure). The surgical instrument 4 also comprises an actuator base 43, which is provided at the end of the instrument shaft 41 and is connected to an end effector 42, wherein the end effector 42 is connected to the actuator base 43 through a drive shaft, and the drive shaft is a pitch shaft 44 extending along the X-axis or a deflection shaft extending along the Y-axis. The surgical instrument 4 further comprises a movable connecting section 45, which is configured between the instrument shaft 41 and the actuator base 43, and is connected to the instrument shaft 41 and the actuator base 43 respectively through movable joints 46. The movable joints 46 have freedoms of movement in the X-axis, the Y-axis and the Z-axis. In the initial state (as shown in FIG. 7), the instrument shaft 41, the actuator base 43 and the movable connecting section 45 are coaxial. And when the movable joint 46 moves (in parallel unfolded states as shown in FIG. 8), the spatial position of the actuator base 43 changes while the posture remains unchanged.

The movable connecting section 45 is essentially a parallel mechanism, and its function is to drive its distal end (the actuator base 43 is connected to its distal end) to a certain position in the spherical space, while maintaining the posture of its distal end unchanged relative to its proximate end (the instrument shaft 41 is located at its proximal end). If the proximal pose of the movable connecting section 45 is recorded as (x1, y1, z1; phi1, theta1, psy1), then its distal pose is (x2, y2, f (x2, y2); phi1, theta1, psy1); wherein x, y, and z are used to describe a position, and phi, theta, and psy are used to describe a posture.

In a specific example, the movable joint 46 comprises a gear mechanism, and the pitch movement of the movable connecting section 45 around the X-axis is achieved through the meshing transmission of the gear mechanism, thereby driving the position of the actuator base 43 to change in the Y-axis and the Z-axis. The movable joint 46 also comprises a deflection mechanism. Through the deflection movement of the deflection mechanism, the movable connecting section 45 is deflected around the Y-axis, thereby driving the position of the actuator base 43 to change in the X-axis. The gear mechanism and deflection mechanism can adopt existing mechanisms, and the present invention is not limited thereto.

In this embodiment, the end effector 42 can perform a pitch movement in space around the pitch shaft 44, and the range of the pitch movement is about −90° to +90°. In other embodiments, the end effector 42 and the actuator base 43 can also be connected through a deflection shaft extending along the Y-axis, that is, the pitch shaft 44 is replaced by a deflection shaft extending along the Y-axis, which is not specifically shown in the figure. In addition, driven by the robotic arm, the end effector 42 can deflect in space around the vertical rotation axis R1 (only the direction of the vertical rotation axis R1 is illustrated in FIG. 8, and the actual position of the vertical rotation axis R1 is not located at the marked position). The range of the deflection movement is about −90°~+90°.

The movable connecting section 45 can provide the end effector 42 with freedoms of movement in the X-axis, in the Y-axis, and in the Z-axis. When the movable connecting section 45 is parallelly unfolded, the axis 410 of the instrument shaft 41 is always parallel to the axis 430 of the actuator base 43 in space, so that the posture freedom and the displacement freedom of the end effector 42 are decoupled, reducing control difficulty, and improving movement accuracy.

An embodiment of the present invention also provides a control method for a terminal mechanism of a surgical robot, which can be applied to the terminal mechanism of the surgical robot described in any of the above embodiments. The features and principles of the terminal mechanism of the surgical robot described in any of the above embodiments can be applied to the following control method embodiments. In the following control method embodiments, the features and principles of the terminal mechanism of the surgical robot that have already been explained will not be repeated.

Figure 9:
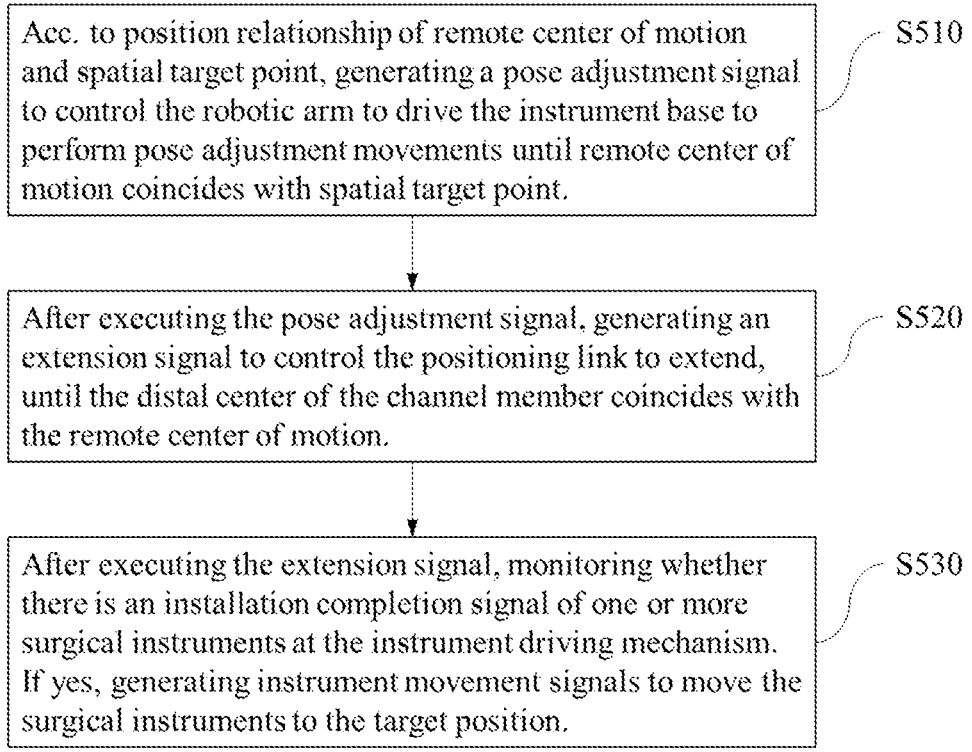
FIG. 9 shows a flow chart of a control method for a terminal mechanism of a surgical robot in an embodiment of the present invention.

FIG. 9 shows the flow of the control method of the terminal mechanism of the surgical robot in an embodiment. Referring to FIG. 9, the control method of the terminal mechanism of the surgical robot comprises the following steps. In step S510, according to the position relationship between the remote center of motion and a spatial target point, a pose adjustment signal is generated for controlling the robotic arm, so that the robotic arm drives the instrument base to perform pose adjustment movements until the remote center of motion coincides with the spatial target point. In step S520, after the execution of the pose adjustment signal is completed, an extension signal is generated to control the positioning link, so that the positioning link extends, until the distal center of the channel member coincides with the remote center of motion. In step S530, after the execution of the extension signal is completed, it is monitored whether there is an installation completion signal of one or more surgical instruments at the instrument driving mechanism. If yes, instrument movement signals are generated to move the surgical instruments to the target position.

The surgical robot is equipped with a controller for generating control signals, and the surgical robot is equipped with an operable control panel, or the surgical robot can be communicatively connected to a computer device, to receive control instructions input by an operator at the control panel or at the computer device. The controller generates control signals to drive the movement of each component. Before generating the pose adjustment signal, the surgical robot can be moved to the vicinity of the spatial target point manually or by inputting control instructions.

The spatial target point can be determined as needed, and is not limited in the present invention. The X-Y-Z coordinate system shown in FIG. 1 can be the base coordinate system of the surgical robot. Through the X-Y-Z coordinate system, the controller of the surgical robot can obtain the position information of each component. Furthermore, according to the positional relationship between the remote center of motion and the spatial target point, and according to the positional relationship between the distal center of the channel member and the remote center of motion, and further according to the positional relationship between the surgical instrument and the target position, the pose adjustment signal, the extension signal, and the instrument movement signals can be generated respectively.

Figure 10:
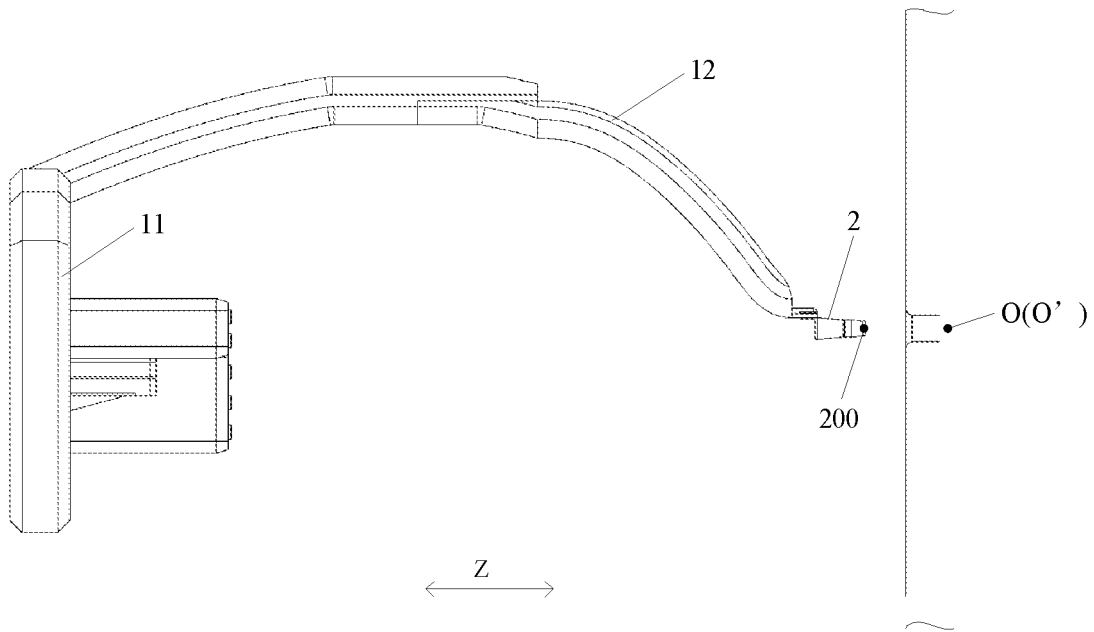
FIG. 10 shows a schematic diagram after executing the pose adjustment signal in an embodiment of the present invention.

FIG. 10 shows a schematic diagram after completing the execution of the pose adjustment signal in an embodiment. Referring to FIG. 10, when the execution of the pose adjustment signal is completed, the remote center of motion O of the surgical robot coincides with the spatial target point O'. During the pose adjustment movements where the robot arm drives the instrument base 11, structural components such as the positioning link 12 remain unchanged in configuration, and the distal center 200 of the channel member 2 faces the remote center of motion O along the Z-axis.

Figure 11:
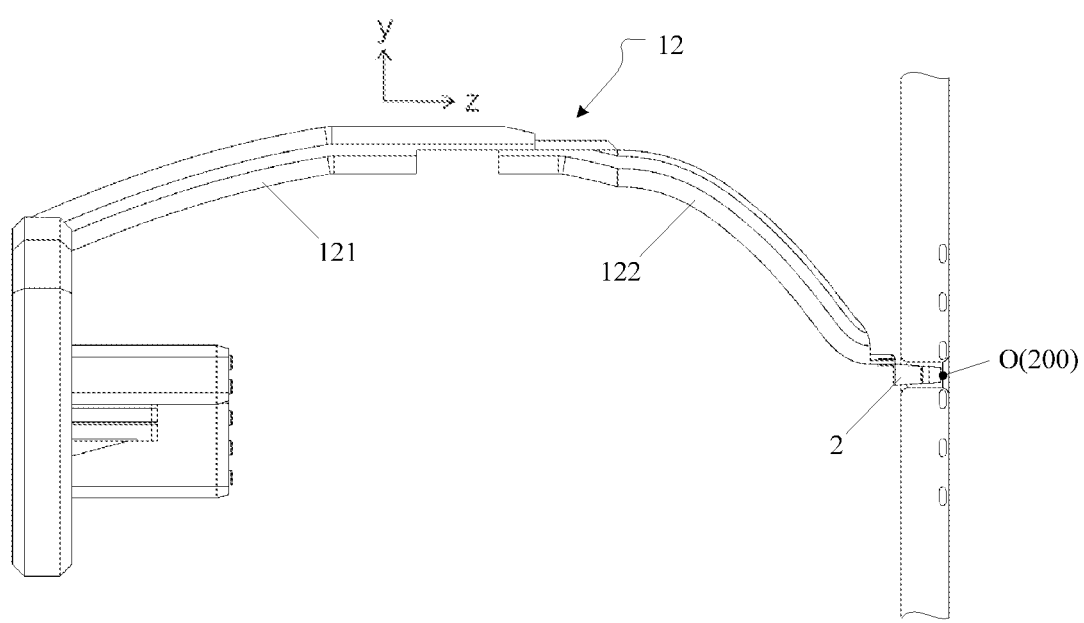
FIG. 11 shows a schematic diagram after executing the extension signal in an embodiment of the present invention.

FIG. 11 shows a schematic diagram after completing the execution of the extension signal in an embodiment. Referring to FIG. 11, when the execution of the extension signal is completed, a second section 122 of the positioning link 12 extends along the Z-axis relative to its first section 121, until the distal center 200 of the channel member 2 coincides with the remote center of motion O. The first section 121 and the second section 122 of the positioning link 12 can be connected through a moving guide rail, so that the second section 122 can move in the Z-axis relative to the first section 121 and drive the channel member 2 to the remote center of motion O.

Figure 12:
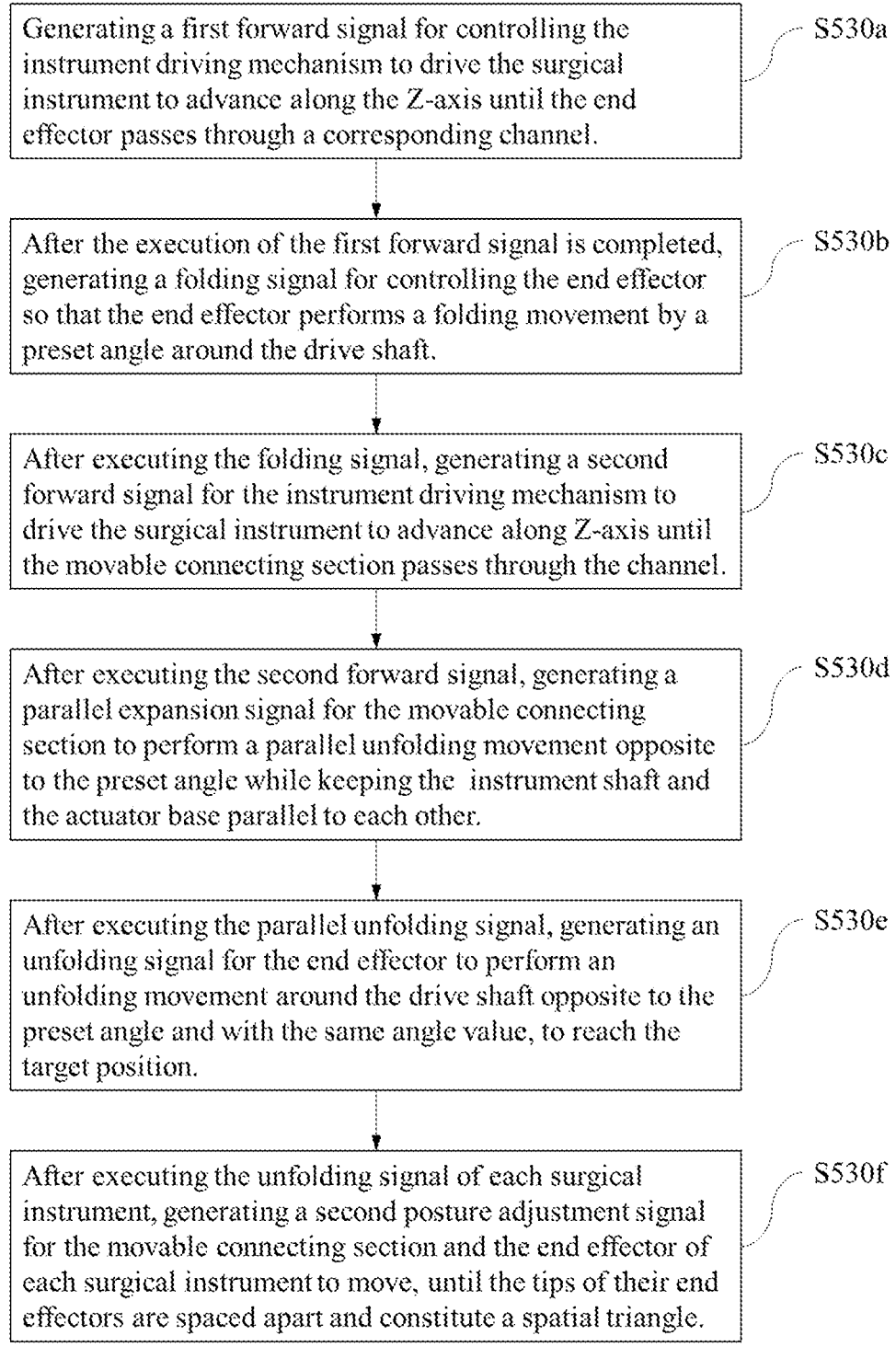
FIG. 12 shows a flow chart for generating instrument motion signals in an embodiment of the present invention.

After the positioning link 12 is extended to the point where its distal center coincides with the remote center of motion, the surgical instruments need to be installed. After the surgical instruments are installed, the controller of the surgical robot can detect the installation completion signal. Each time a surgical instrument is installed, a corresponding instrument movement signal is sent out to move the surgical instrument to the target position. The instrument movement signal comprises control signals respectively used to control the instrument driving mechanism and the surgical instrument. FIG. 12 shows the process of generating the instrument movement signal in one embodiment. Referring to FIG. 12, generating the instrument movement signal comprises the following steps.

In step S530a, a first forward signal is generated for controlling the instrument driving mechanism, so that the instrument driving mechanism drives the surgical instrument to advance along the Z-axis until the end effector passes through a corresponding channel.

Figure 13:
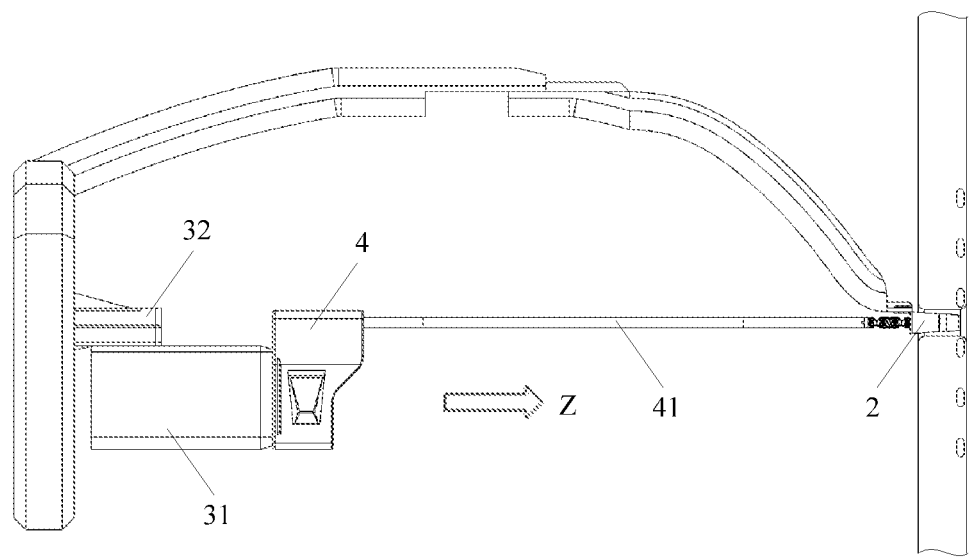
FIG. 13 shows a schematic diagram of executing the first forward signal in an embodiment of the present invention.
Figure 14:
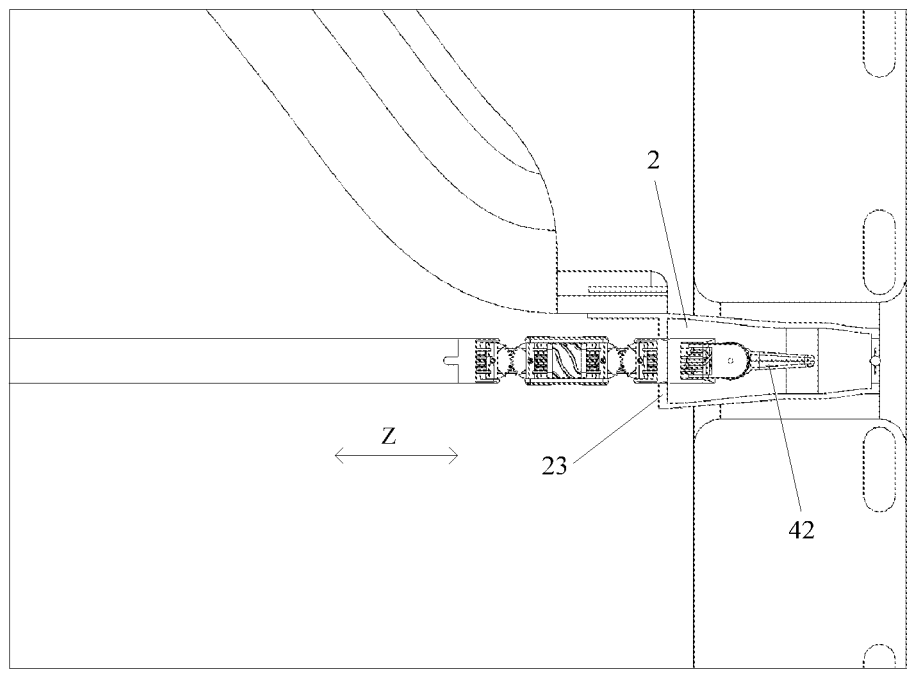
FIG. 14 shows a partial perspective view of FIG. 13.

FIG. 13 shows a schematic diagram of the first forward signal being executed in an embodiment, and FIG. 14 shows a partial perspective diagram of FIG. 12. 13 and FIG. 14, the moving mechanism 32 of the instrument driving mechanism can drive the instrument driving module 31 to move along the Z-axis, and then drive the surgical instrument 4 to advance in parallel along the Z-axis under the control of the first advance signal, until the end effector 42 connected to the end of the instrument shaft 41 passes through the proximal end plate 23 of the channel member 2, to enter the interior of the channel member 2.

Figure 15:
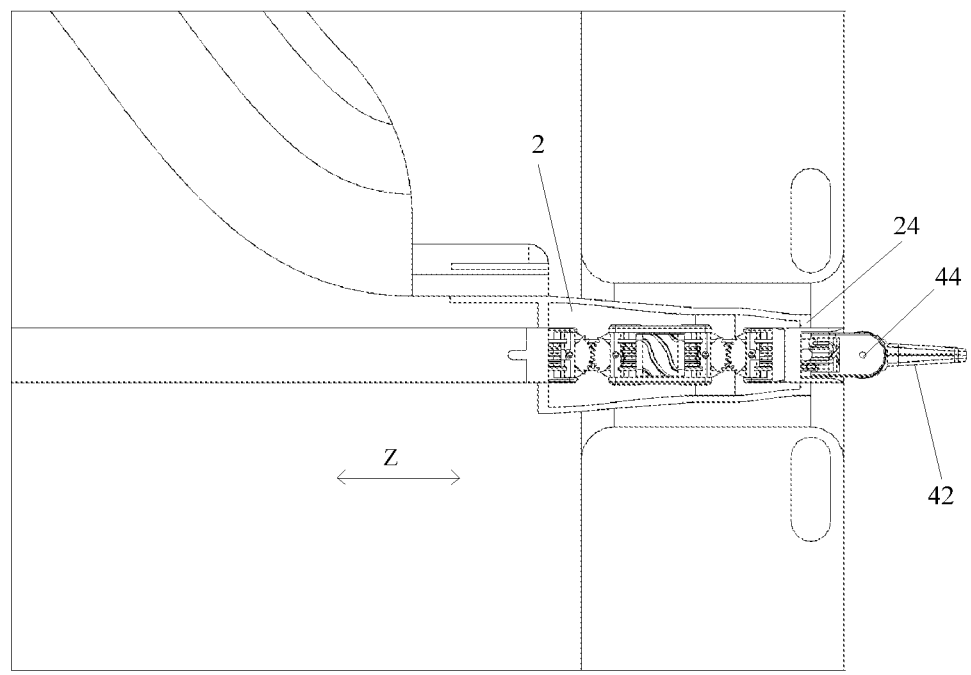
FIG. 15 shows a schematic diagram after executing the first forward signal in an embodiment of the present invention.

FIG. 15 shows a schematic diagram after completing the execution of the first forward signal. As shown in FIG. 13 to FIG. 15, under the control of the first forward signal, the moving mechanism 32 continues to drive the instrument driving module 31 to advance along the Z-axis, thereby driving the end effector 42 to pass through the distal end plate 24 of the channel member 2, until the pitch shaft 44 passes through the distal end plate 24, and then the movement of the instrument driving mechanism in the Z-axis stops.

When the end effector 42 is connected to the actuator base through a deflection shaft, then, under the control of the first forward signal, the movement of the instrument driving mechanism in the Z-axis stops when the end effector 42 and the deflection shaft pass through the distal end plate 24.

In step S530b, after the execution of the first forward signal is completed, a folding signal for controlling the end effector is generated so that the end effector performs a folding movement by a preset angle around the drive shaft.

Figure 16:
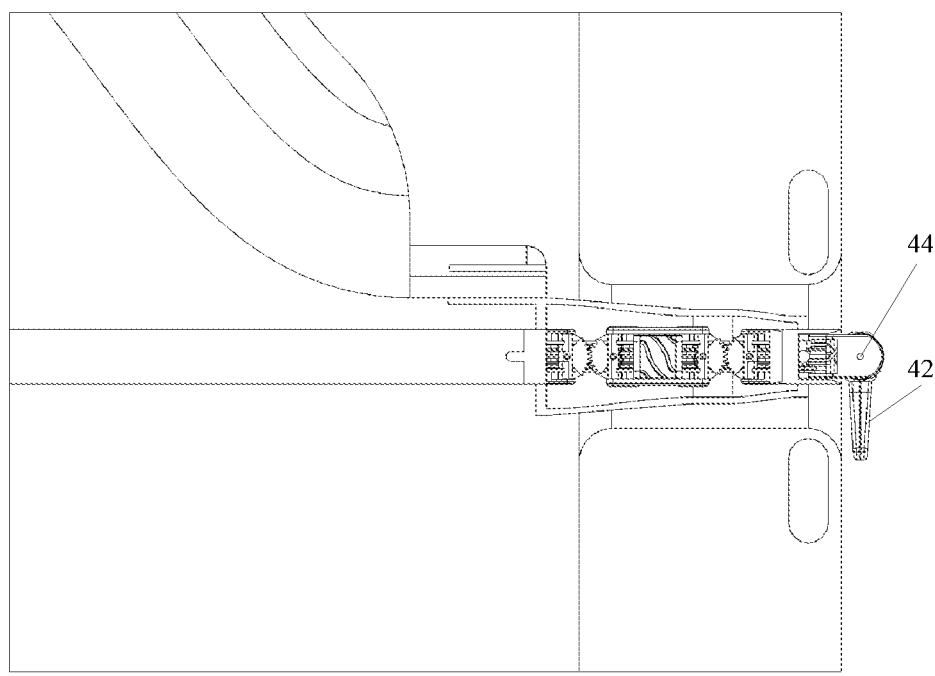
FIG. 16 shows a schematic diagram after executing a folding signal in an embodiment of the present invention.

FIG. 16 shows a schematic diagram after completing the execution of the folding signal in one embodiment. Referring to FIG. 16, when the drive shaft is a pitch shaft 44, the end effector 42 can perform a pitch movement around the pitch shaft 44, and the folding movement around the pitch shaft 44 is called a first pitch movement. Specifically, under the control of the folding signal, the end effector 42 makes a pitch movement upward or downward around the pitch shaft 44. The pitch angle can be any angle between −90° and +90° to reduce the projected length of the surgical instrument on its own axis, to avoid interference with other components during movement. FIG. 16 shows that the end effector 42 is pitched downward by 90° around the pitch shaft 44, but is not limited thereto.

In other embodiments, when the drive shaft is a deflection shaft, the folding motion is called a first deflection movement around the deflection shaft, and the deflection angle can be any angle between −90° and +90°. For example, the end effector 42 can be deflected 90° to the left around the deflection shaft, but not limited to this.

In step S530c, after the execution of the folding signal is completed, a second forward signal is generated for controlling the instrument driving mechanism, so that the instrument driving mechanism drives the surgical instrument to advance along the Z-axis until the movable connecting section passes through the corresponding channel.

Figure 17:
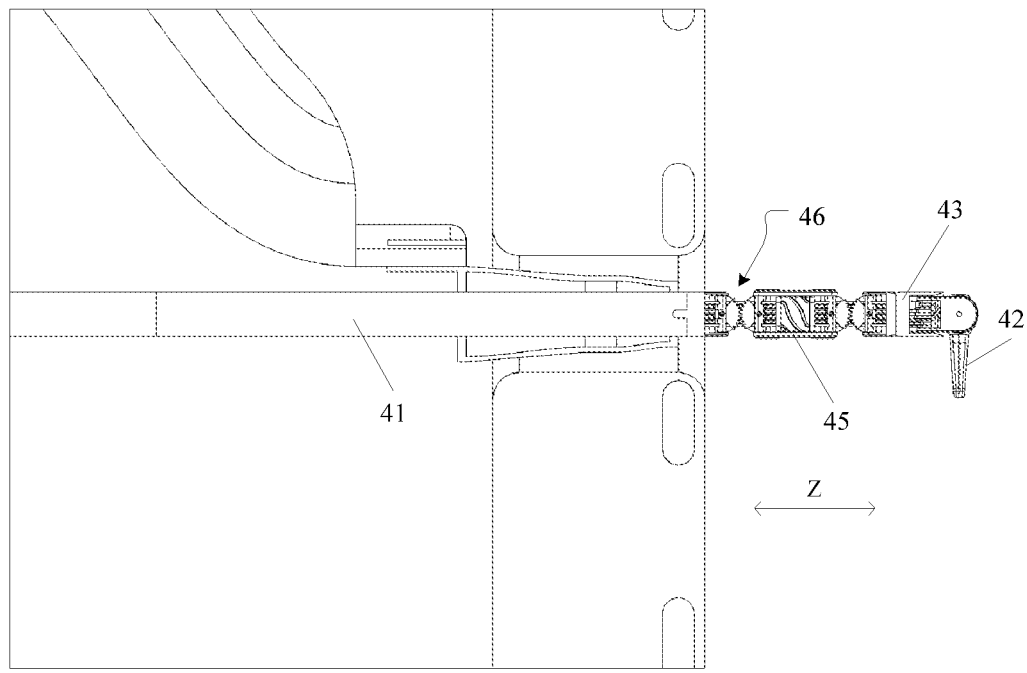
FIG. 17 shows a schematic diagram after executing the second forward signal in an embodiment of the present invention.

FIG. 17 shows a schematic diagram after completing the execution of the second forward signal in an embodiment. Referring to FIG. 17, the instrument shaft 41 of the surgical instrument and the actuator base 43 are connected through movable connecting section 45. In the initial state, the instrument shaft 41, the actuator base and the movable connecting section 45 are coaxial. After the end effector 42 is folded, the movable connecting section 45 continues to be pushed forward. Under the control of the second forward signal, the instrument driving mechanism continues to drive the surgical instrument forward in the Z-axis until the movable joint 46 connecting the movable connecting section 45 and the instrument shaft 41 passes through the corresponding channel. During the process of advancing the movable connecting section 45, the movable connecting section 45 always remains coaxial with the instrument shaft 41, and the posture of the end effector 42 remains unchanged to avoid interference between components.

In step S530d, after the execution of the second forward signal is completed, a parallel expansion signal for controlling the movable connecting section 45 is generated, so that the movable connecting section 45 performs a parallel unfolding movement in an opposite direction of the preset angle direction, and during the parallel unfolding process, the instrument shaft and the actuator base keep parallel to each other.

Figure 18:
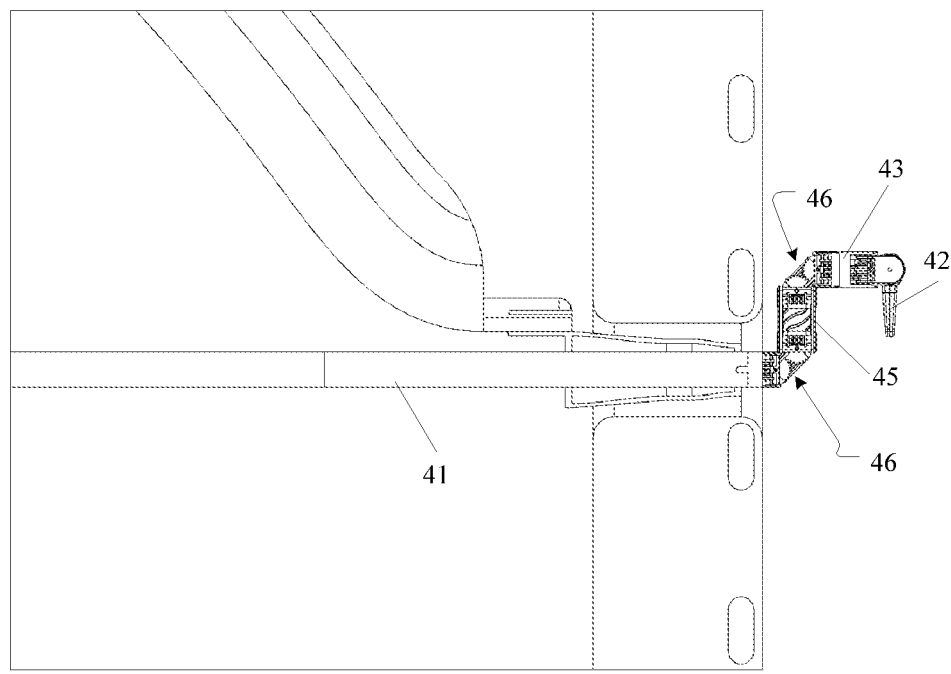
FIG. 18 shows a schematic diagram after executing the parallel unfolding signal in an embodiment of the present invention.

FIG. 18 shows a schematic diagram after executing the parallel unfolding signal in one embodiment. Referring to FIG. 18, there are movable joints 46 between the movable connecting section 45 and the instrument shaft 41, as well as between the movable connecting section 45 and the actuator base 43, respectively. The movable joints have freedoms of movement around the X-axis, around the Y-axis, and around the Z-axis. When the drive shaft is a pitch shaft, the parallel unfolding signal is a pitch unfolding signal, and the parallel unfolding movement is called a second pitch movement around the X-axis. Specifically, under the control of the pitch unfolding signal, the movable connecting section 45 can move upward or downward. The pitch direction is opposite to the pitch direction of the end effector 42 in step S530b, so as to reduce the occupied space and to avoid interference with other components. Specifically, the movable connecting section 45 can be pitched and unfolded in a 90° manner as shown in FIG. 18, but is not limited to this.

In other embodiments, when the drive shaft is a deflection shaft, the parallel unfolding signal is a deflection unfolding signal, and the parallel unfolding movement is called a second deflection movement around the Y-axis. Specifically, under the control of the deflection unfolding signal, the movable connecting section 45 can deflect to the left or right, and its deflection direction is opposite to the deflection direction of the end effector in step S530b, so as to reduce the occupied space and to avoid interference with other components.

During the parallel unfolding movement of the movable connecting section 45, the instrument shaft 41 and the actuator base 43 always remain parallel, so that the posture freedom and displacement freedom of the end effector 42 are decoupled, reducing control difficulty and improving movement accuracy.

In step S530e, after the execution of the parallel unfolding signal is completed, an unfolding signal for controlling the end effector is generated, so that the end effector performs an unfolding movement around the drive shaft in the opposite direction to the preset angle and with the same angle value, to reach the target position.

Figure 19:
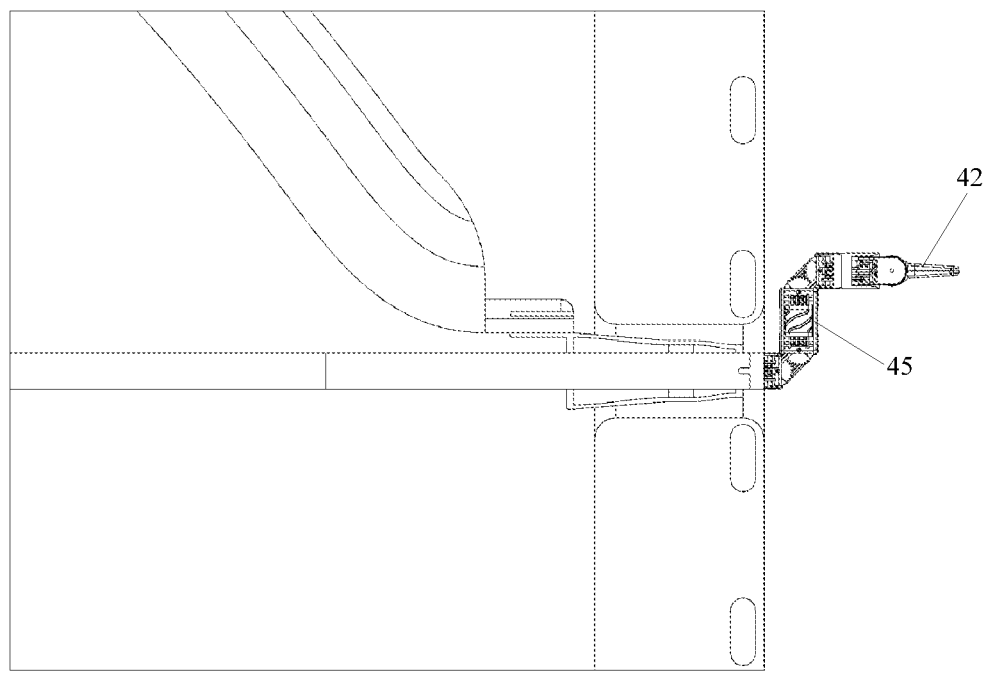
FIG. 19 shows a schematic diagram after executing the unfolding signal in an embodiment of the present invention.

FIG. 19 shows a schematic diagram after executing the unfolding signal in one embodiment. Referring to FIG. 19, when the drive shaft is a pitch shaft, the unfolding movement is called a third pitch movement around the pitch shaft, so that the pitching angle of the end effector 42 formed in step S530b is reset to zero, and the target position is reached. In other embodiments, when the drive shaft is a deflection shaft, the unfolding movement is called a third deflection motion around the deflection shaft, so that the deflection angle of the end effector deflected and folded in step S530b is reset to zero, to reach the target position.

From step S530a to step S530e, the control of the surgical instruments is completed. When the controller of the surgical robot detects multiple installation completion signals, it repeats the above steps S530a to S530e to control each surgical instrument.

When the instrument driving mechanism is equipped with two surgical instruments, the process of generating the instrument movement signals also comprises the following step: after the execution of the unfolding signal of each surgical instrument is completed, a first posture adjustment signal is generated for controlling the movable connecting section and the end effector of each surgical instrument. The first posture adjustment signals are used to move the surgical instruments until the tips of their end effectors are spaced from each other and opposed to each other.

Further, when the instrument driving mechanism is equipped with three surgical instruments, the process of generating instrument movement signals also comprises: referring to step S530f shown in FIG. 12, after the execution of the unfolding signal of each surgical instrument is completed, a second posture adjustment signal is generated for controlling the movable connecting section and the end effector of each surgical instrument. The second posture adjustment signal controls the surgical instruments to move, until the tips of their end effectors are spaced apart and constitute a spatial triangle.

Figure 20:
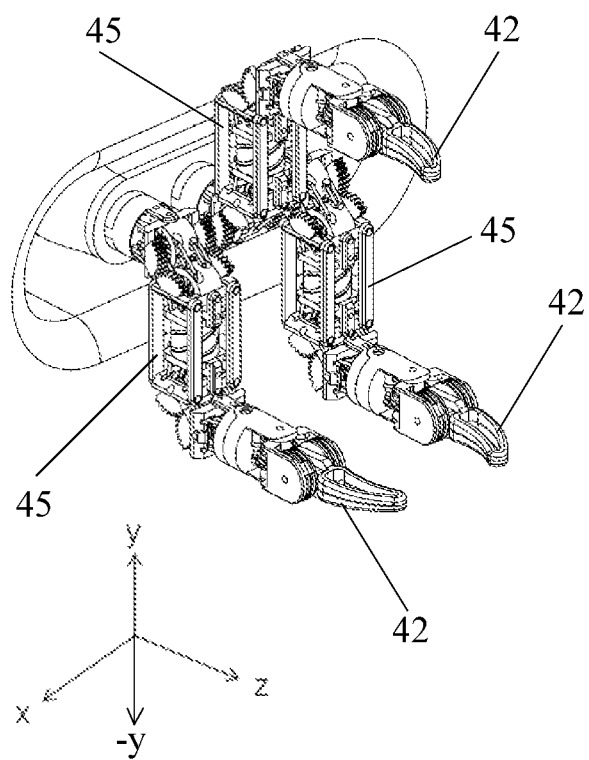
FIG. 20 shows a schematic diagram after executing the unfolding signals of three surgical instruments in an embodiment of the present invention.

FIG. 20 shows a schematic diagram after executing the unfolding signals of three surgical instruments in one embodiment. Referring to FIG. 20, when the unfolding signals of the three surgical instruments are all completed, the movable connecting section 45 of each surgical instrument is unfolded and the end effector 42 is flattened. FIG. 20 shows that the movable connecting sections 45 of three surgical instruments are respectively unfolded in the −Y direction, in the +Y direction and in the −Y direction, but are not limited to this. In other embodiments, all the movable connecting sections 45 of the three surgical instruments can also be unfolded in the +Y direction, or all in the −Y direction, or respectively in the +Y direction, in the −Y direction and in the +Y direction, without interfering with each other.

Figure 21:
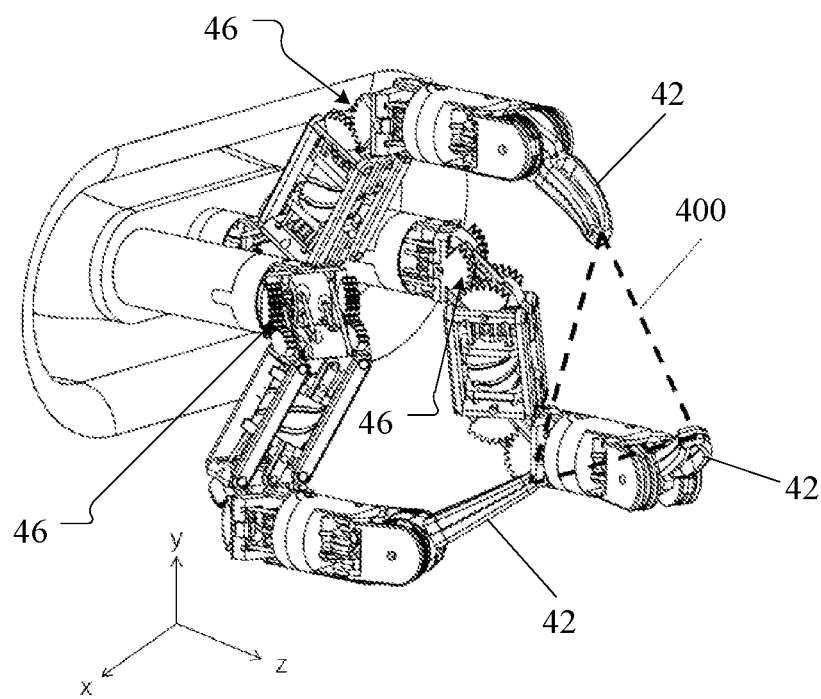
FIG. 21 to FIG. 23 show schematic diagrams after executing the second posture adjustment signal in an embodiment of the present invention.
Figure 22:
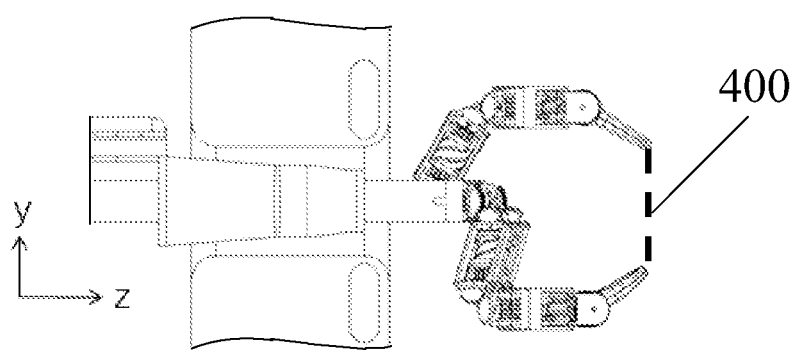
Figure 23:
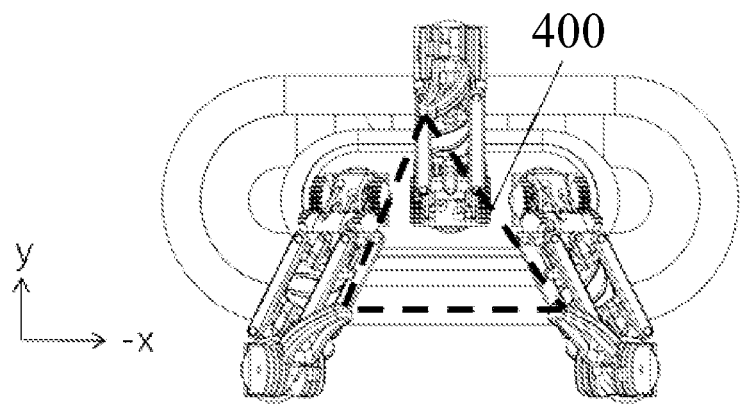

FIG. 21 to FIG. 23 show a schematic diagram after executing the second posture adjustment signals in an embodiment. Referring to FIG. 21 to FIG. 23, in addition to providing freedoms of movement in the Z-axis and in the Y-axis, the movable joints 46 can also provide freedom of movement in the X-axis. Under the control of the second posture adjustment signal, the movable joint 46 of each surgical instrument can perform spatial position movement, and each surgical instrument can also perform posture adjustment, so that the three surgical instruments move to the configuration where the tips of their end effectors 42 are relatively spaced apart, and form a spatial triangle 400. FIG. 22 shows that the tips of the end effectors of the three surgical instruments are located on a same plane parallel to the Y-axis, but this is not a limitation. The end effectors of the three surgical instruments only need to have their tips spaced apart from each other and form a spatial triangle 400.

All of the above controlling steps, except for the manual operation required to install the surgical instruments, can be executed step by step and automatically by the controller of the surgical robot. The operator may monitor and evaluate the process and the results of each step, and confirm whether to perform the next operation. The operator may interrupt the control operation at any time during the control process, that is, the above-mentioned pose adjustment signals, extension signals, and equipment movement signals can all be interrupted. When a control signal is interrupted, the execution of the corresponding control signal is suspended, and the execution of the corresponding control signal is continued when a continuing instruction is detected. Thus, not only is the convenience of using the surgical robot improved, enabling the operator to adjust the execution progress at any time as needed during the entire control process, but also the stability and availability of the surgical robot are ensured. After the operator confirms to continue the execution, the surgical robot will continue to execute automatically according to the preset control process without causing damage to the surgical robot.

During the execution of each control signal, the execution status of the executing object is monitored. When an error or exception is detected in the execution status, the execution completion status of the previous control signal of the current control signal is restored, to wait for a re-execution instruction. Thus, when a failure or exception is detected in a subsequent step, the process can return to the previous step and wait for further instruction signals.

Further, every time after a control signal is executed, the corresponding executing object is locked. For example, after the pose adjustment signal is executed, the robot arm is locked, and after the extension signal is executed, the positioning link is locked to achieve independent and precise control between components and avoid interference.

In another embodiment different from the process shown in FIG. 12, before advancing the surgical instrument along the Z-axis, the movable connecting section and the end effector of the surgical instrument can be driven to move so that the surgical instrument forms a certain predefined configuration, and then the surgical instrument is advanced by the moving mechanism of the instrument driving mechanism.

Specifically, the step of generating instrument movement signals comprises: generating a first movement signal for controlling the surgical instrument so that the end effector moves in the Y-axis and/or the Z-axis to a predefined configuration relative to the instrument axis. After the execution of the first motion signal is completed, a second motion signal is generated for controlling the instrument driving mechanism, so that the instrument driving mechanism drives the surgical instrument to move along the Y-axis and/or the Z-axis, until the end effector and the end of the instrument shaft go through the corresponding channel and reach the target position.

The movement of the end effector can be driven by the movable connecting section and the actuator base, and the instrument driving mechanism can drive the surgical instrument through its moving mechanism. This has been described in detail above and will not be repeated here.

Figure 24:
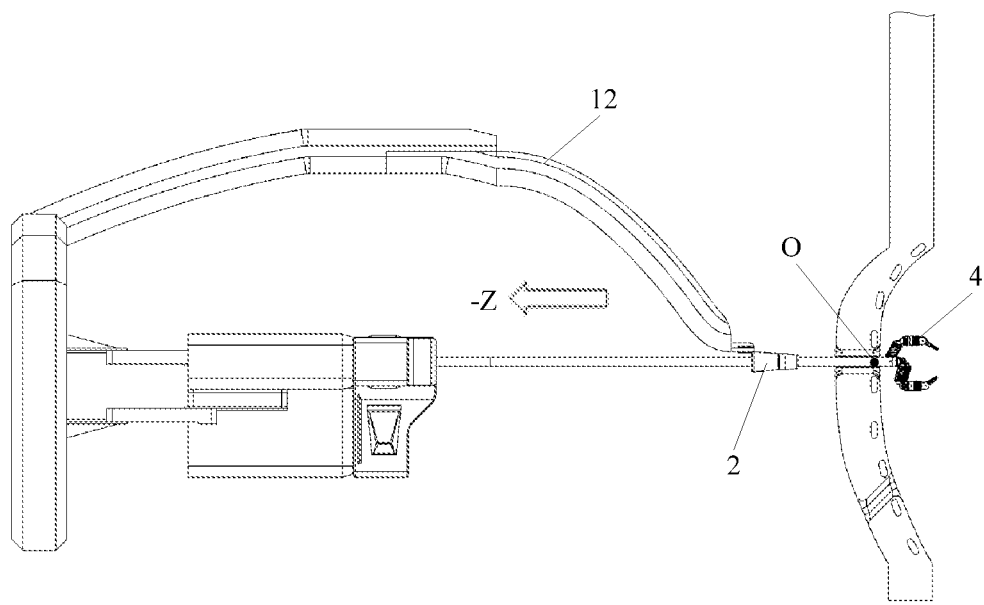
FIG. 24 shows a schematic diagram after executing the retraction signal in an embodiment of the present invention.

Further, the control method also comprises the following step: when the surgical instrument moves to the target position, a retraction signal is generated for controlling the positioning link, so that the positioning link is retracted until the distal center of the channel member is facing the remote center of motion. FIG. 24 shows a schematic diagram after executing the retraction signal in an embodiment. Referring to FIG. 24, when the surgical instrument 4 reaches the target position, the positioning link 12 drives the channel member 2 to retract parallel to the −Z direction, to keep a safe distance from the remote center of motion O. When and only when a single, part or all of the surgical instruments 4 need to be replaced, the positioning link 12 can move parallel to the +Z direction again under the action of a control signal, driving the channel member 2 to move toward the remote center of motion O. Through this configuration, the interference and disturbance of the channel member 2 upon the remote center of motion O can be minimized.

After the execution of the retraction signal is completed, a control signal for unlocking the robotic arm and the instrument driving mechanism can be generated, to allow the robotic arm to drive the instrument base for pose adjustment movement upon a trigger signal, and to allow the instrument driving mechanism to drive the surgical instrument upon a trigger signal.

Figure 25:
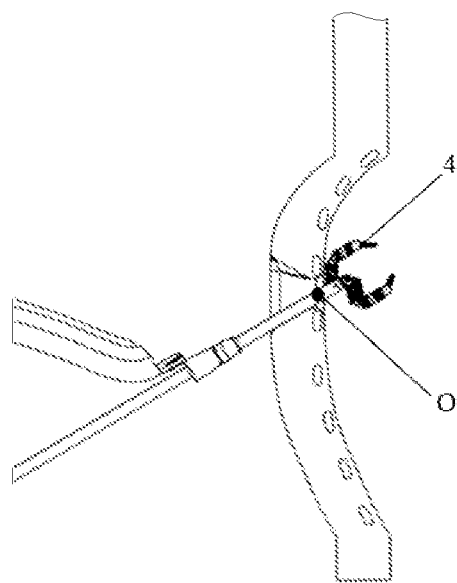
FIG. 25 and FIG. 26 show a schematic diagram of the robotic arm driving the surgical instrument to pitch after the robotic arm is unlocked.
Figure 26:
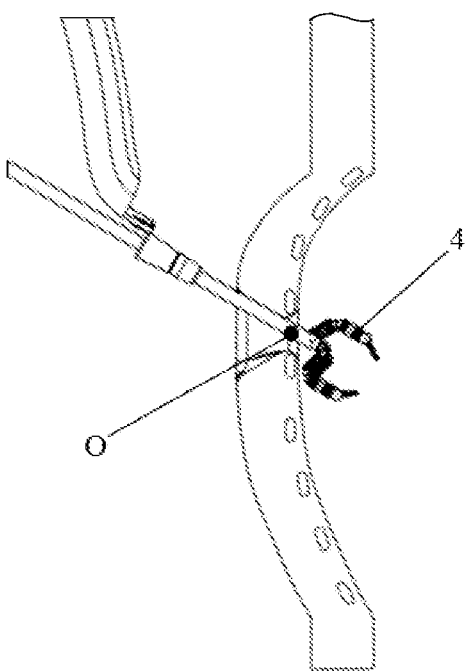

FIG. 25 and FIG. 26 show a schematic diagram of the robotic arm driving the surgical instrument to pitch after the robotic arm is unlocked. Referring to FIG. 25 and FIG. 26, after the surgical instrument 4 reaches the target position, if the surgical instrument 4 still needs to perform a pitch movement, an operator may trigger the robotic arm. For example, pitch-related operating instructions may be input at the control panel of the surgical robot, then the robotic arm can provide a degree of freedom of pitching for the surgical instrument 4, to drive the surgical instrument 4 to pitch upward relative to the remote center of motion O, as shown in FIG. 25, or, to pitch downward relative to the remote center of motion O, as shown in FIG. 26. At this point, in order to avoid interference between the pitch motion of the surgical instrument 4 and the components at the target position, the pitch angle is preferably in the range of −45° to +45°.

Figure 27:
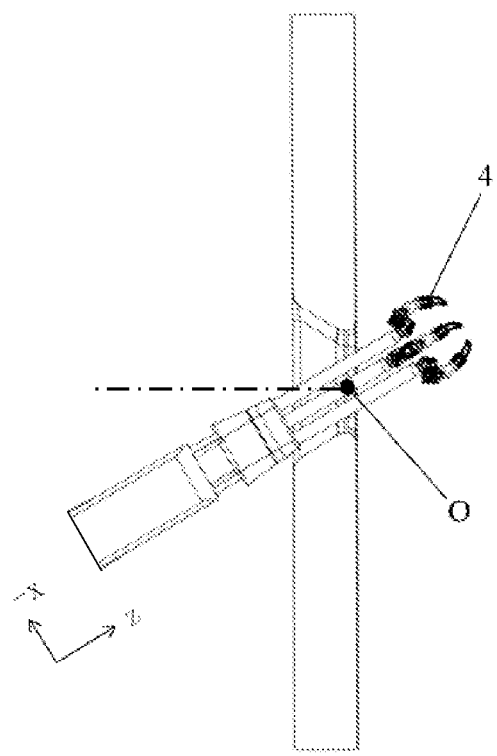
FIG. 27 and FIG. 28 show a schematic diagram of the robotic arm driving the surgical instrument to deflect after the robotic arm is unlocked.
Figure 28:
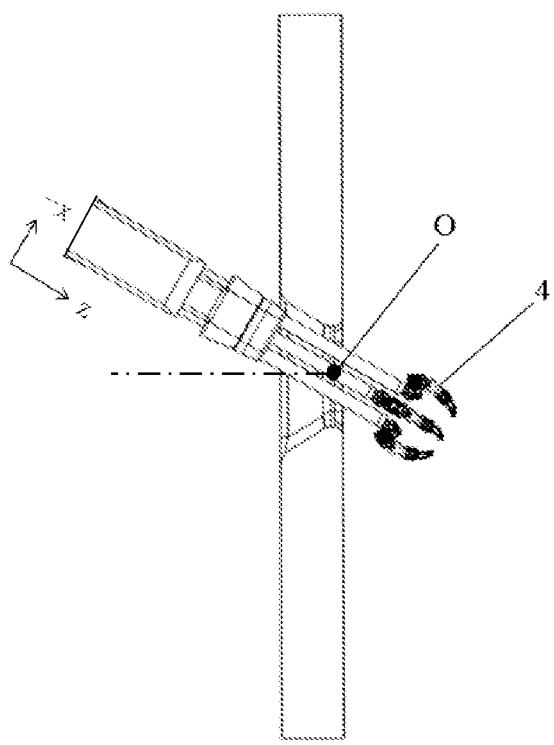

FIG. 27 and FIG. 28 show a schematic diagram of the robotic arm driving the surgical instrument to deflect after the robotic arm is unlocked. Referring to FIG. 27 and FIG. 28, after the surgical instrument 4 reaches the target position, if the surgical instrument 4 still needs to deflect, the robotic arm can be triggered by an operator, for example, by inputting deflection-related operating instructions at the control panel of the surgical robot. The robotic arm can provide a deflection freedom of movement for the surgical instrument 4, to drive the surgical instrument 4 to rotate around the vertical rotation axis where the remote center point O is located, so that the surgical instrument 4 is deflected to the left as shown in FIG. 27, or to the right as shown in FIG. 28. At this point, in order to avoid interference between the deflection motion of the surgical instrument 4 and the components at the target position, the deflection angle is preferably in the range of −30° to +30°.

Figure 29:
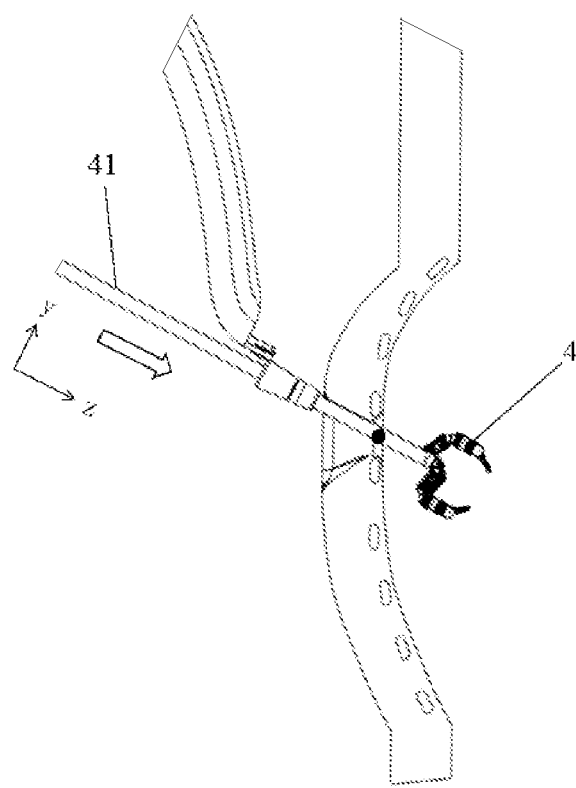
FIG. 29 shows a schematic diagram of the instrument driving mechanism driving the movement of the surgical instrument after the instrument driving mechanism is unlocked.

FIG. 29 shows a schematic diagram of the instrument driving mechanism driving the surgical instrument to move after the instrument driving mechanism is unlocked. Referring to FIG. 29, after the surgical instrument 4 reaches the target position, if the surgical instrument 4 still needs to move in the direction of the instrument shaft 41, the operator may trigger the instrument driving mechanism, for example, by inputting advance and retreat related operating instructions at the control panel of the surgical robot. The instrument driving mechanism can provide the surgical instrument 4 with a degree of freedom in the forward and retreat direction. For example, comparing FIG. 29 with FIG. 26, the surgical instrument 4 is driven by the instrument driving mechanism to a deeper position along the Z-axis.

The above control method is used to control the terminal mechanism of the surgical robot to avoid interference of end parts, to improve control accuracy, and to ensure the stability and availability of the surgical robot, without causing damage to the surgical robot, and to ensure the safety of the surgical robot during use as well as to improve the case of use.

An embodiment of the present invention also provides a control device for a terminal mechanism of a surgical robot, which can be used to implement the control method described in any of the above embodiments. The features and principles of the control method described in any of the above embodiments can be applied to the following control device embodiments. In the following control device embodiments, the features and principles of the control process of the terminal mechanism of the surgical robot that have already been explained will not be repeated.

Figure 30:
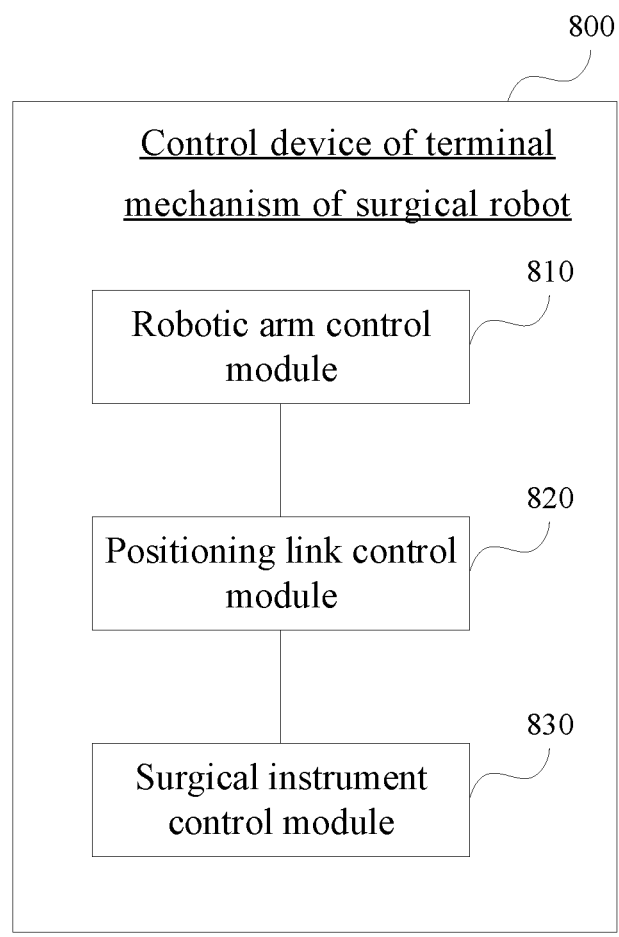
FIG. 30 shows a module diagram of a control device of a terminal mechanism of a surgical robot in an embodiment of the present invention.

FIG. 30 shows the modules of the control device of the terminal mechanism of the surgical robot in one embodiment. Referring to FIG. 30, the control device 800 of the terminal mechanism of the surgical robot comprises a robotic arm control module 810, configured to generate a pose adjustment signal for controlling the robotic arm, according to the positional relationship between the remote center of motion and the spatial target point, so that the robotic arm drives the instrument base to perform pose adjustment movements, until the remote center of motion coincides with the spatial target point. The control device 800 also comprises a positioning link control module 820, configured to generate an extension signal for controlling the positioning link after the pose adjustment signal is executed, so that the positioning link extends, until the distal center of the channel member coincides with the remote center of motion. The control device 800 further comprises a surgical instrument control module 830, configured to monitor whether there is an installation completion signal between the instrument driving mechanism and a surgical instrument after the execution of the extension signal. If an installation completion signal is detected, an instrument movement signal is generated to move the surgical instrument to the target position.

Further, the control device 800 may also comprise modules that implement other process steps of the above control method embodiments. For the specific principles of each module, reference can be made to the description of the above control method embodiments, and the description will not be repeated here.

The control device 800 may specifically be a controller of the surgical robot, or a part of the controller. The control device 800 can control the terminal mechanism of the surgical robot, to avoid interference of end components, to improve control accuracy, to ensure the stability and usability of the surgical robot, and will not cause damage to the surgical robot, and can ensure the safety of the surgical robot during use, and improve the case of use.

An embodiment of the present invention also provides an electronic device, comprising a processor and a memory. The memory stores executable instructions. When the executable instructions are executed by the processor, the control method of the terminal mechanism of the surgical robot described in any of the above embodiments is implemented.

Figure 31:
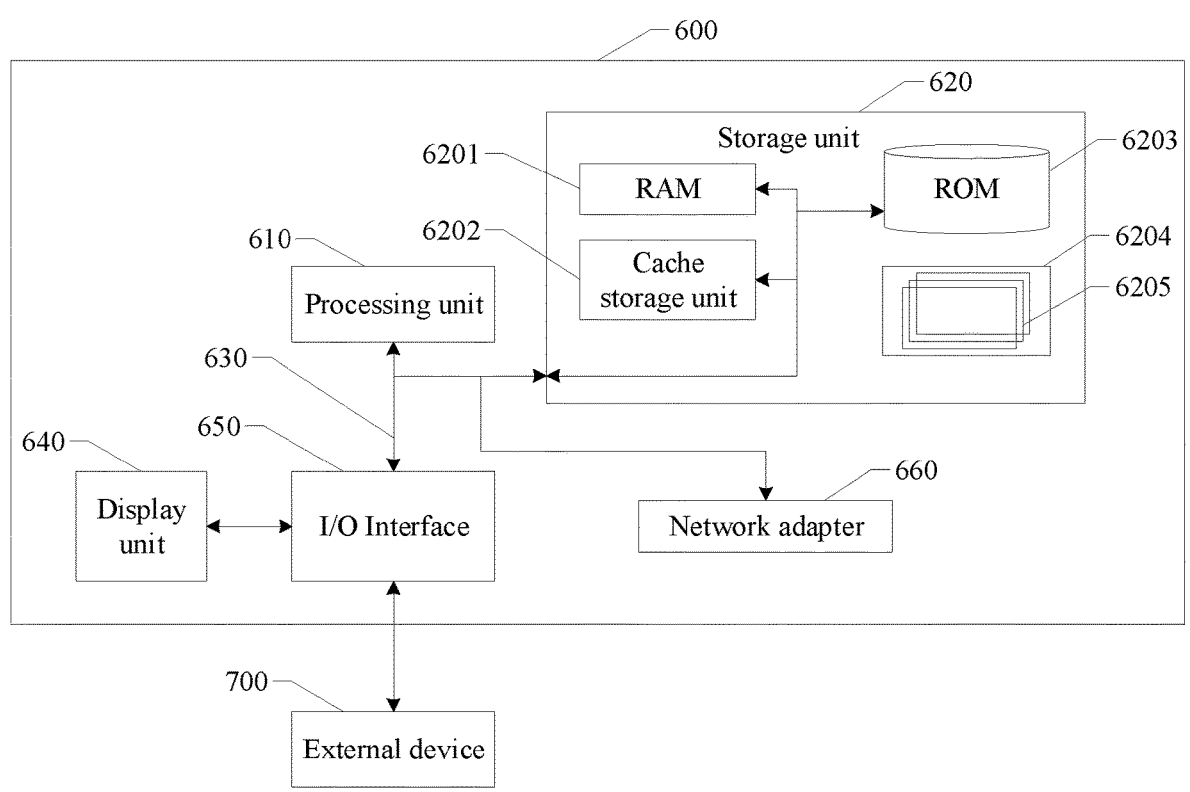
FIG. 31 shows a structural diagram of an electronic device in an embodiment of the present invention.

FIG. 31 shows the structure of an electronic device in an embodiment. It should be understood that FIG. 31 only schematically shows various modules. These modules can be virtual software modules or actual hardware modules. The merging and division of these modules, the addition of other modules are all within the protection scope of the present invention.

As shown in FIG. 31, electronic device 600 is embodied in the form of a general computing device. The components of the electronic device 600 comprise, but are not limited to: at least one processing unit 610, at least one storage unit 620, a bus 630 connecting different platform components (including the storage unit 620 and the processing unit 610), a display unit 640, and so on.

The storage unit 620 stores program code, which can be executed by the processing unit 610 to cause the processing unit 610 to perform the steps of the control method for the terminal mechanism of the surgical robot described in any of the above embodiments. For example, the processing unit 610 may perform the steps shown in FIG. 9 and FIG. 12.

The storage unit 620 may comprise a readable medium in the form of a volatile storage unit, such as a random-access storage unit (RAM) 6201 and/or a cache storage unit 6202, and may further comprise a read-only storage unit (ROM) 6203.

Storage unit 620 may also comprise a program/utility subunit 6204 having one or more program modules 6205. Such program modules 6205 include, but are not limited to: an operating system, one or more application programs, other program modules, and program data, examples of each of these, or some combination thereof, may include the implementation of a network environment.

Bus 630 may be one or more of several types of bus structures, including a memory unit bus or memory unit controller, a peripheral bus, a graphics acceleration port, a processing unit, or a local bus using any of a variety of bus structures.

The electronic device 600 may also communicate with one or more external devices 700, which may be one or more of a keyboard, a pointing device, a Bluetooth device, and other devices. These external devices 700 enable users to interact and communicate with the electronic device 600. Electronic device 600 can also communicate with one or more other computing devices, including routers and modems. Such communication may occur through input/output (I/O) interface 650. Furthermore, the electronic device 600 may also communicate with one or more networks, e.g., a local area network (LAN), a wide area network (WAN), and/or a public network, such as the Internet, through the network adapter 660. Network adapter 660 may communicate with other modules of electronic device 600 via bus 630. It should be understood that, although not shown in the figures, other hardware and/or software modules may be used in conjunction with electronic device 600, including but not limited to: microcode, device drivers, redundant processing units, external disk drive arrays, RAID systems, tape drives, and data backup storage platforms, etc.

The electronic device 600 may specifically be a controller of the surgical robot, or a part of the controller. The electronic device 600 can control the terminal mechanism of the surgical robot, to avoid interference of end components, to improve control accuracy, to ensure the stability and usability of the surgical robot, to avoid causing damage to the surgical robot, and to ensure the safety of the surgical robot during use, and to improve the case of use.

Embodiments of the present invention also provide a computer-readable storage medium for storing a program. When the program is executed, the control method for the terminal mechanism of a surgical robot described in any of the above embodiments is implemented. In some possible implementations, various aspects of the present invention can also be implemented in the form of a program product, which comprises program code. When the program product is run on a terminal device, the program code is used to cause the terminal device to perform the control method described in any of the above embodiments.

The program product may take the form of a portable compact disk read-only memory (CD-ROM) and comprise program code, and may be run on a terminal device, such as a personal computer. However, the program product of the present invention is not limited thereto, and may be any tangible medium containing or storing a program, which may be used by or in combination with an instruction execution system, apparatus or device.

The Program Product may take the form of one or more readable media in any combination. The readable medium may be a readable signal medium or a readable storage medium. The readable storage medium may be, for example, but not limited to, an electrical, magnetic, optical, electromagnetic, infrared, or semiconductor system, device or apparatus, or any combination thereof. More specific examples of readable storage media include, but are not limited to: electrical connections with one or more wires, portable disks, hard disks, random access memory (RAM), read only memory (ROM), erasable programmable read only memory (EPROM or flash memory), optical fiber, portable compact disk read-only memory (CD-ROM), optical storage device, magnetic storage device, or any suitable combination of the above.

The readable storage medium may comprise a data signal propagated in baseband or as part of a carrier wave carrying the readable program code therein. Such propagated data signals may take many forms, including but not limited to electromagnetic signals, optical signals, or any suitable combination of the above. A readable storage medium may also be any readable medium other than a readable storage medium that can transmit, propagate, or transport the program for use by or in connection with an instruction execution system, apparatus, or device. Program code contained on a readable storage medium may be transmitted using any suitable medium, including but not limited to wireless, wired, optical cable, RF, etc., or any suitable combination of the above.

Program code for performing the operations of the present invention may be written in any combination of one or more programming languages, including object-oriented programming languages such as Java, C++, etc., as well as conventional procedural programming languages, such as "C" or similar programming languages. The program code may execute entirely on the user's computing device, partly on the user's device, as a stand-alone software package, partly on the user's computing device and partly on a remote computing device, or entirely on a remote computing device or server. In situations involving remote computing devices, the remote computing device may be connected to the user computing device through any kind of network, including a local area network (LAN) or a wide area network (WAN), or may be connected to an external computing device via internet connection, such as that provided by an internet service business.

The storage medium can be configured in the controller of the surgical robot to control the terminal mechanism of the surgical robot when it is executed, avoiding interference of end components, improving control accuracy, ensuring the stability and availability of the surgical robot, and not causing damage to the surgical robot. It can ensure the safety of the surgical robot during use and improve the convenience of use.

The above content is a further detailed description of the present invention in combination with specific preferred embodiments, and it cannot be concluded that the specific implementation of the present invention is limited to these descriptions. For those of ordinary skill in the technical field to which the present invention belongs, several simple deductions or substitutions can be made without departing from the concept of the present invention, and all of them should be regarded as belonging to the protection scope of the present invention.

The invention claimed is:

1. A terminal mechanism of a surgical robot, characterized by comprising:
    an instrument base, connected to a distal end of a robotic arm of the surgical robot, wherein the robotic arm is configured to drive the instrument base to perform pose adjustment movements relative to a remote center of motion defined by the robotic arm; and,
    a positioning link, configured to telescope along a Z-axis, and connected to the instrument base, wherein a distal end of the positioning link is configured to hold a channel member, and the channel member is provided with multiple channels, and each channel extends along the Z-axis, and a distal center of the channel member faces the remote center of motion along the Z-axis;
    wherein the channel member comprises: a hollow shell, clamped to the distal end of the positioning link through a connecting buckle; and, a proximal end plate and a distal end plate, respectively provided at a proximal end of the hollow shell facing the positioning link and a distal end away from the positioning link, wherein the proximal end plate and the distal end plate are respectively provided with through-hole arrays constituting the multiple channels; and wherein each through-hole array is distributed in a same height layer referring to a Y-axis to form a one-row array along an X-axis, or, each through-hole array is distributed in multiple height layers referring to a Y-axis to form a multiple-row array with each row of through-holes arranged along an X-axis; and,
    an instrument driving mechanism, configured to install and drive multiple surgical instruments and connected to the instrument base, wherein multiple instrument installation paths and driving paths of the instrument driving mechanism do not interfere with each other, and when the instrument driving mechanism is installed with multiple surgical instruments, instrument shafts of the multiple surgical instruments extend along the Z-axis and align with the multiple channels respectively;
    wherein, the instrument driving mechanism comprises multiple instrument driving modules used to install and drive the multiple surgical instruments respectively, and the multiple instrument driving modules are connected to the instrument base by multiple moving mechanisms respectively, and the moving mechanisms are configured to drive the instrument driving modules to move along the Y-axis and the Z-axis respectively; wherein, the pose adjustment movements comprise a pitch movement and a yaw movement around a vertical rotation axis passing through the remote center of motion.

2. The terminal mechanism of claim 1, wherein the surgical instrument comprises:
    an instrument shaft, connected to the instrument driving mechanism through a transmission device; and,
    an actuator base, provided at a distal end of the instrument shaft and installed with an end effector, wherein the end effector is connected to the actuator base through a drive shaft, wherein the drive shaft is a pitch shaft extending along an X-axis, or a deflection shaft extending along a Y-axis; and,
    a movable connecting section, located between the instrument shaft and the actuator base, and connected to the instrument shaft and the actuator base through movable joints respectively, wherein the movable joints have freedoms of movement around the X-axis, the Y-axis and the Z-axis;
    wherein, in an initial state, the instrument shaft, the actuator base and the movable connecting section are coaxial, and with the moving of the movable joints, a spatial position of the actuator base changes while its posture remains unchanged.

3. A control method for a terminal mechanism of a surgical robot, characterized in that,
    the control method is applicable to the terminal mechanism according to claim 1, and comprises:
    generating a pose adjustment signal for controlling the robotic arm according to a positional relationship between the remote center of motion and a spatial target point, so that the robotic arm drives the instrument base to perform the pose adjustment movements, until the remote center of motion coincides with the spatial target point; and,
    generating an extension signal to control the positioning link after executing the pose adjustment signal, so that the positioning link extends, until the distal center of the channel member coincides with the remote center of motion; and, monitoring whether there is an installation completion signal of a surgical instrument at the instrument driving mechanism after executing the extension signal; and, if yes, generating instrument movement signals to move the surgical instrument to a target position.

4. The control method according to claim 3, wherein, the instrument driving mechanism is configured to move along the Z-axis, and a distal end of an instrument shaft is provided with an actuator base, and the actuator base is connected with an end effector; and, said generating instrument movement signals comprises:

generating a first forward signal for controlling the instrument driving mechanism, so that the instrument driving mechanism drives the surgical instrument to advance along the Z-axis until the end effector passes through a corresponding channel.

5. The control method according to claim 4, wherein, the end effector and the actuator base are connected through a drive shaft, and the drive shaft is a pitch shaft extending along an X-axis or a deflection shaft extending along a Y-axis, and the first forward signal is used to advance the surgical instrument until the drive shaft passes through the corresponding channel; and, said generating instrument movement signals further comprises:

after executing the first forward signal, generating a folding signal to control the end effector, so that the end effector performs a folding movement by a preset angle around the drive shaft;

wherein, when the drive shaft is a pitch shaft, the folding movement is a first pitch movement around the pitch shaft, and when the drive shaft is a deflection shaft, the folding movement is a first deflection movement around the deflection shaft.

6. The control method according to claim 5, wherein, a movable connecting section is connected between the instrument shaft and the actuator base, and in an initial state, the movable connecting section is coaxial with the instrument shaft and the actuator base; and, said generating instrument movement signals further comprises:

after executing the folding signal, generating a second forward signal to control the instrument driving mechanism, so that the instrument driving mechanism drives the surgical instrument to advance along the Z-axis until the movable connecting section passes through the corresponding channel.

7. The control method according to claim 6, wherein, movable joints are provided between the movable connecting section and the instrument shaft, and between the movable connecting section and the actuator base respectively, and the movable joints have freedoms of movement along the X-axis, the Y-axis and the Z-axis, and the second forward signal is used to advance the surgical instrument until the movable joints pass through the corresponding channel; and, said generating instrument movement signals further comprises:

after executing the second forward signal, generating a parallel unfolding signal to control the movable connecting section, so that the movable connecting section performs a parallel unfolding movement in an opposite direction of the preset angle, and during all steps of the parallel unfolding movement, the actuator base remains parallel to the instrument shaft;

wherein, when the drive shaft is a pitch shaft, the parallel unfolding movement is a second pitch movement around the X-axis, and when the drive shaft is a deflection shaft, the parallel unfolding movement is a second deflection movement around the Y-axis.

8. The control method according to claim 7, wherein, said generating instrument movement signals further comprises:

after executing the parallel unfolding signal, generating un unfolding signal to control the end effector, so that the end effector performs an unfolding movement around the drive shaft in an opposite direction of the preset angle and by an angle equal to the preset angle, to reach the target position;

wherein, when the drive shaft is a pitch shaft, the unfolding movement is a third pitch movement around the pitch shaft, and when the drive shaft is a deflection shaft, the unfolding movement is a third deflection movement around the deflection shaft.

9. The control method according to claim 8, wherein, when the instrument driving mechanism is equipped with two surgical instruments, said generating an instrument movement signal further comprises:

after executing the unfolding signal of each surgical instrument, generating first posture adjustment signals to control the movable connecting section and the end effector of each surgical instrument, so that the surgical instruments move to positions where tips of the end effectors are opposed to each other and are spaced from each other.

10. The control method according to claim 8, wherein, when the instrument driving mechanism is equipped with three surgical instruments, said generating an instrument movement signal further comprises:

after executing the unfolding signal of each surgical instrument, generating second posture adjustment signals to control the movable connecting section and the end effector of each surgical instrument, so that the surgical instruments move to positions where tips of the end effectors are opposed to each other and constitute a spatial triangle.

11. The control method according to claim 3, wherein, the pose adjustment signal, the extension signal and the equipment movement signals are all configured to be interruptible, wherein when a signal is interrupted, a corresponding execution of the signal is paused, until when a continuing signal is detected, the corresponding execution of the signal is continued; and, during an execution of a current signal, an execution status of an executing object is monitored, wherein, when the execution status of the executing object is abnormal, an execution completion status of a preceding signal of the current signal is restored, to wait for a re-execution instruction; and, after execution of the current signal, a corresponding executing object is locked and waits for a subsequent signal.

12. The control method according to claim 3, wherein, the instrument driving mechanism is configured to move along a Y-axis and the Z-axis, and an end effector is provided at a distal end of an instrument shaft, and spatial positions in the Y-axis and in the Z-axis of the end effector are variable; and, said generating instrument movement signals comprises:

generating a first movement signal to control the surgical instrument, so that the end effector moves along a plane defined by the Y-axis and the Z-axis, to a predefined configuration relative to the instrument shaft; and, after executing the first movement signal, generating a second movement signal to control the instrument driving mechanism, so that the instrument driving mechanism drives the surgical instrument to move along the plane defined by the Y-axis and the Z-axis until the end effector and the distal end of the instrument shaft pass through a corresponding channel and reach the target position.

13. The control method according to claim 3, further comprising:

generating a retraction signal to control the positioning link when the surgical instrument moves to the target position, so that the positioning link is retracted until the distal center of the channel member faces the remote center of motion.

14. A control device for a terminal mechanism of a surgical robot, characterized in that, the control device is used to implement the control method according to claim 3, and the control device comprises:

a robotic arm control module, configured to generate the pose adjustment signal to control the robotic arm according to a positional relationship between a remote center of motion and a spatial target point, so that the robotic arm drives the instrument base to perform the pose adjustment movements, until the remote center of motion coincides with the spatial target point; and, a positioning link control module, configured to generate the extension signal to control the positioning link after executing the posture adjustment signals, so that the positioning link extends, until the distal center of the channel member coincides with the remote center of motion; and, a surgical instrument control module, configured to monitor whether there is an installation completion signal of a surgical instrument at the instrument driving mechanism after executing the extension signal, and if yes, to generate the instrument movement signals to move the surgical instrument to the target position.

\* \* \* \* \*